US012678434B2

(12) United States Patent
Mubarak et al.

(10) Patent No.: US 12,678,434 B2
(45) Date of Patent: Jul. 14, 2026

(54) COMPOSITIONS AND METHODS FOR MODULATING ACE2 RECEPTOR

(71) Applicants: Kamal Khan Mubarak, Ann Arbor, MI (US); Eman Azra Mubarak, Ann Arbor, MI (US)

(72) Inventors: Kamal Khan Mubarak, Ann Arbor, MI (US); Eman Azra Mubarak, Ann Arbor, MI (US)

( * ) Notice: Subject to any disclaimer, the term of this patent is extended or adjusted under 35 U.S.C. 154(b) by 775 days.

(21) Appl. No.: 17/917,984

(22) PCT Filed: Apr. 12, 2021

(86) PCT No.: PCT/US2021/026860

§ 371 (c)(1),
(2) Date: Oct. 10, 2022

(87) PCT Pub. No.: WO2021/207729

PCT Pub. Date: Oct. 14, 2021

(65) Prior Publication Data

US 2023/0142221 A1 May 11, 2023

Related U.S. Application Data

(60) Provisional application No. 63/008,226, filed on Apr. 10, 2020.

(51) Int. Cl.

| | |
|---|---|
| ***A61K 31/495*** | (2006.01) |
| ***A61K 31/138*** | (2006.01) |
| ***A61K 31/335*** | (2006.01) |
| ***A61K 31/341*** | (2006.01) |
| ***A61K 31/4164*** | (2006.01) |
| ***A61K 31/426*** | (2006.01) |
| ***A61K 31/4402*** | (2006.01) |
| ***A61K 31/445*** | (2006.01) |
| ***A61K 31/4535*** | (2006.01) |
| ***A61K 31/4545*** | (2006.01) |
| ***A61K 31/55*** | (2006.01) |
| ***A61P 31/14*** | (2006.01) |

(52) U.S. Cl.
CPC .......... *A61K 31/495* (2013.01); *A61K 31/138* (2013.01); *A61K 31/335* (2013.01); *A61K 31/341* (2013.01); *A61K 31/4164* (2013.01); *A61K 31/426* (2013.01); *A61K 31/4402* (2013.01); *A61K 31/445* (2013.01); *A61K 31/4535* (2013.01); *A61K 31/4545* (2013.01); *A61K 31/55* (2013.01); *A61P 31/14* (2018.01)

(58) Field of Classification Search
CPC .................................................... A61K 31/495
See application file for complete search history.

(56) References Cited

U.S. PATENT DOCUMENTS

| | | | | |
|---|---|---|---|---|
| 6,028,094 A * | 2/2000 | Nakashima | ........ | A61K 31/4174 514/399 |
| 2008/0159962 A1 | 7/2008 | Penninger et al. | | |
| 2011/0159001 A1 | 6/2011 | Lanzavecchia | | |
| 2013/0085124 A1 | 4/2013 | May | | |
| 2019/0224164 A1 | 7/2019 | Bodor | | |

FOREIGN PATENT DOCUMENTS

WO 2018042343 A2 3/2018

OTHER PUBLICATIONS

Gangadevi et al. CAS: 174:449498, 2021.*
Javanmard et al. CAS: 172: 500888, 2020.*
International Search Report and Written Opinion of PCT/US2021/026860 mailed Aug. 2, 2021, 15 pages.

* cited by examiner

*Primary Examiner* — Rei Tsang Shiao
(74) *Attorney, Agent, or Firm* — Lowenstein Sandler LLP

(57) ABSTRACT

Disclosed in certain embodiments are compositions and methods for treating coronavirus related adverse events with an angiotensin-converting enzyme 2 (ACE2) receptor modulator.

6 Claims, 14 Drawing Sheets

D: Diphenhydramine
RC: R-Cetirizine
RA: R-Azelastine
H: Hydroxyzine

COMPOSITIONS AND METHODS FOR MODULATING ACE2 RECEPTOR

CROSS-REFERENCE TO RELATED APPLICATION SECTIONS

The present application is a national stage entry under 35 U.S.C. § 371 of International Application No. PCT/US2021/026860, filed on Apr. 12, 2021, which claims priority to U.S. Provisional Patent Application No. 63/008,226, filed on Apr. 10, 2020, the contents of which are hereby incorporated by reference in their entirety.

FIELD OF THE INVENTION

The present disclosure is directed to pharmaceutical compositions and methods directed at modulating angiotensin-converting enzyme 2 (ACE2) receptors to treat coronavirus and adverse events caused by it (such as severe acute respiratory syndrome (SARS), middle eastern respiratory syndrome (MERS), coronavirus disease 2019 (COVID-19), and the like).

BACKGROUND OF THE INVENTION

Angiotensin-converting enzyme 2 (ACE2) is an ectoenzyme attached to the cell membranes of cells in the lungs, arteries, heart, kidneys, and intestines. ACE2 is a membrane-bound aminopeptidase and is expressed in high levels by pulmonary endothelial cells. ACE2 is also a functional receptor for certain coronaviruses that cause severe acute respiratory syndrome (SARS).

Certain coronaviruses are believed to gain entry into certain cells, such as pulmonary endothelial cells, by membrane fusion on binding to ACE2. For instance, the entry of coronavirus, SARS-CoV and SARS-CoV-2, into pulmonary endothelial cells is believed to occur through interaction of SARS-CoV and SARS-CoV-2 with ACE2. This interaction is believed to be mediated by the SARS-CoV and SARS-CoV-2 spike proteins.

Symptoms associated with coronavirus infections, such as SARS and COVID-19, are very severe, life-threatening, and in certain instances deadly. There exists a need in the art for new therapies for the prevention, treatment, and/or amelioration of coronavirus infections and symptoms associated with such infections.

OBJECTS AND SUMMARY OF THE INVENTION

It is an object of certain embodiments of the present invention to provide pharmaceutical compositions for the treatment, prevention, or amelioration of coronavirus related adverse events (e.g., severe acute respiratory syndrome (SARS)).

It is an object of certain embodiments of the present invention to provide methods for the treatment or prevention of coronavirus related adverse events (e.g., severe acute respiratory syndrome (SARS)).

The above objects and others are met by the present invention which in certain embodiments is directed to a method of treating coronavirus related adverse events comprising administering to a patient in need thereof a therapeutically effective amount of an angiotensin-converting enzyme 2 (ACE2) receptor modulator.

In other embodiments, the invention is directed to a pharmaceutical composition comprising a therapeutically effective amount of an angiotensin-converting enzyme 2 (ACE2) receptor modulator to reduce one or more coronavirus related adverse events.

BRIEF DESCRIPTION OF THE DRAWINGS

The above and other features of the present invention, their nature, and various advantages will become more apparent upon consideration of the following detailed description, taken in conjunction with the accompanying drawings, in which.

DEFINITIONS

Figure 1:
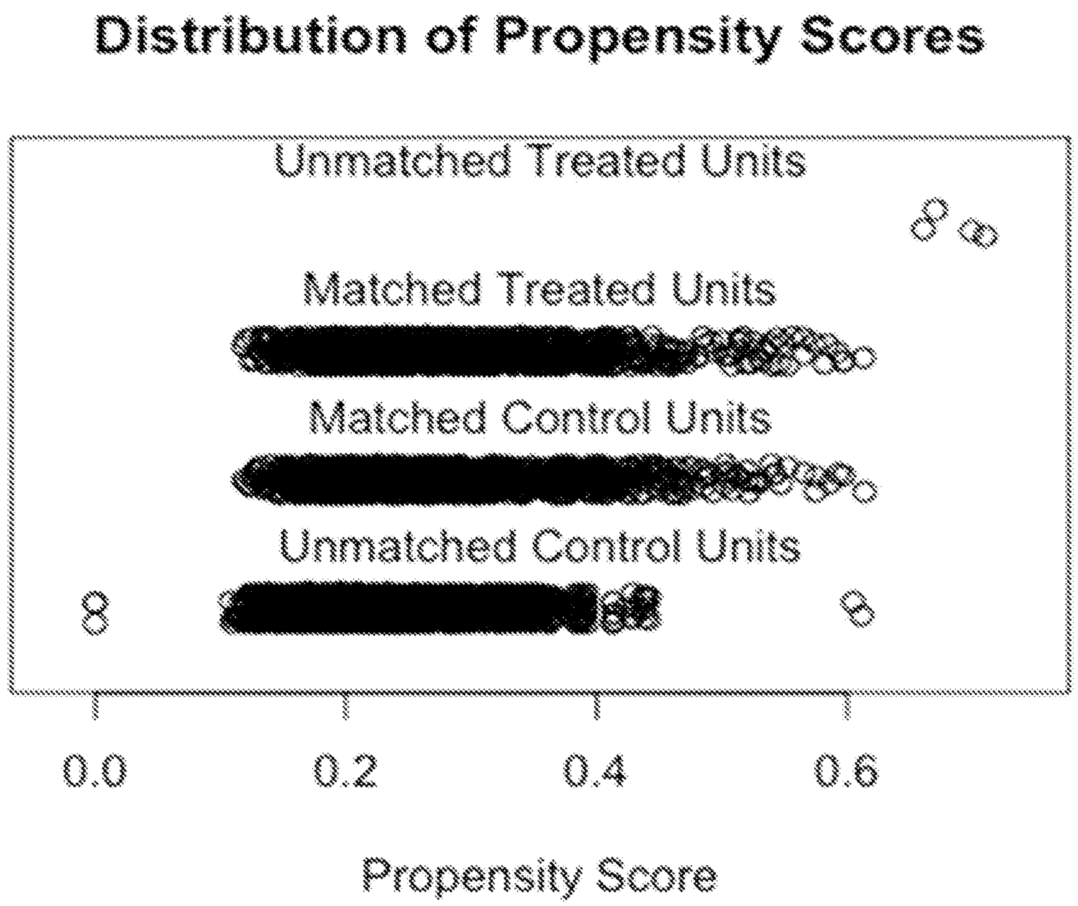
FIG. 1 illustrates distribution of propensity scores in the matched any antihistamine groups (H1 or H2).

As used herein, the singular forms "a," "an," and "the" include plural references unless the context clearly indicates otherwise. Thus, for example, reference to "a drug" includes a single drug as well as a mixture of two or more different drugs, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number±10%, such that "about 10" would include from 9 to 11.

As used herein, a "patient" refers to a subject, particularly a human (but could also encompass a non-human), who has presented a clinical manifestation of a particular symptom or symptoms suggesting the need for treatment, who is treated prophylactically for a condition, or who has been diagnosed with a condition to be treated.

The term "subject" encompasses the definition of the term "patient" and does not exclude individuals who are otherwise healthy.

The terms "treatment of" and "treating" include the administration of a drug with the intent to lessen the severity of or prevent a condition and is not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

The terms "prevention of" and "preventing" include (1) inhibiting or avoiding the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "condition" or "conditions" refers to those medical conditions, such as severe acute respiratory syndrome (SARS), COVID-19, MERS, and the like, that can be treated, mitigated or prevented by administration to a subject of an effective amount of a drug. The term "condition" or "conditions" may also refer to adverse events related to certain medical conditions, such as adverse events related to SARS, adverse events related to coronavirus, adverse events related to MERS, and the like, that can be treated, mitigated or prevented by administration to a subject of an effective amount of a drug.

An "effective amount" refers to the amount of an active agent that is sufficient to produce a beneficial or desired effect at a level that is readily detectable by a method commonly used for detection of such an effect. In some embodiments, such an effect results in a change of at least 10% from the value of a basal level where the active agent is not administered. In other embodiments, the change is at least 20%, 50%, 80%, or an even higher percentage from the basal level. As will be described below, the effective amount of an active agent may vary from subject to subject, depending on age, general condition of the subject, the severity of the condition being treated, the particular active agent administered and the like. An appropriate "effective" amount in any individual case may be determined by one of ordinary skill in the art by reference to the pertinent texts and literature and/or by using routine experimentation.

As used herein, the terms "active agent" or "drug" refer to any material that is intended to produce a therapeutic, prophylactic, or other intended effect, whether or not approved by a government agency for that purpose.

In structures wherein stereochemistry is not explicitly indicated, it is assumed that either stereochemistry is considered and both isomers claimed.

Any undefined valency on an atom of a structure shown in this application implicitly represents a hydrogen atom bonded to the atom.

An "isomer" of a first compound is a separate compound in which each molecule contains the same constituent atoms as the first compound, but where the configuration of those atoms in three dimensions differs.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

The term "Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. In a specific embodiment, the term "pharmaceutically acceptable" means approved by a regulatory agency of the federal or a state government or listed in the U.S. Pharmacopeia or other generally recognized pharmacopeia for use in animals, and more particularly in humans.

"Pharmaceutically acceptable salts" or "salts" means salts of compounds of the present invention which are pharmaceutically acceptable, as defined above, and which possess the desired pharmacological activity. Such salts include acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Pharmaceutically acceptable salts also include base addition salts which may be formed when acidic protons present are capable of reacting with inorganic or organic bases. Suitable pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glutamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the invention. *Handbook of Pharmaceutical Salts: Properties, and Use* (P. H. Stahl & C. G. Wermuth eds., Verlag Helvetica Chimica Acta, 2002) [1].

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods

DETAILED DESCRIPTION

In certain embodiments, the present invention is directed to a method of reducing, preventing, treating, or ameliorating coronavirus and/or one or more of its related adverse events, the method comprising administering to a patient in need thereof a therapeutically effective amount of an ACE2 receptor modulator.

In certain embodiments, the ACE2 receptor modulator may be administered prophylactically before a patient experiences coronavirus related adverse events associated with coronavirus. For instance, the ACE2 receptor modulator may be administered about 48 hours, about 36 hours, about 24 hours, about 12 hours, about 10 hours, about 8 hours, about 6 hours, about 4 hours, about 3 hours, about 2 hours, about 1 hour, or about 0.5 hours before the onset of coronavirus related adverse events or before first coming into contact with an individual having or suspected to have coronavirus (e.g., in the case of first responders or medical professionals treating coronavirus patients).

In other embodiments, the ACE2 receptor modulator may be administered in response to a coronavirus infection and/or to coronavirus related adverse events. For instance, the ACE2 receptor modulator may be administered about 0.5 hour, about 1 hour, about 2 hours, about 3 hours, about 4 hours, about 6 hours, about 8 hours, about 10 hours, about 12 hours, about 24 hours, about 36 hours, or about 48 hours after the onset of coronavirus related adverse events or after first coming into contact with an individual having or suspected to have coronavirus (e.g., in the case of first responders or medical professionals treating coronavirus patients).

The term "coronavirus," as used herein, refers to a group of viruses that cause disease in mammals and birds. In humans, the coronavirus causes respiratory tract infections that can range from mild to lethal. Exemplary coronaviruses include, without limitations, severe acute respiratory syndrome coronavirus (SARS-CoV), human coronavirus NL63 (HCoV-NL63), human coronavirus HKU1 (HCoV-HKU1), middle east respiratory syndrome related coronavirus (MERS-CoV), severe acute respiratory syndrome coronavirus 2 (SARS-CoV-2), and the like. In one embodiment, coronavirus as used herein refers to SARS-CoV-2 which causes coronavirus disease 2019 (COVID-19).

In certain embodiments, the ACE2 receptor modulator is administered in an effective amount to prevent, treat, ameliorate, or reduce one or more coronavirus related adverse events. The coronavirus related adverse events may be one or more of, e.g., pulmonary (e.g., severe acute respiratory syndrome (SARS)), cardiac, dermatologic, gastrointestinal, renal, hepatic, endocrine, neurological, or a combination thereof.

In one embodiment, the ACE2 receptor modulator is administered in an effective amount to prevent, treat, ameliorate, or reduce COVID-19 and its related adverse events or symptoms caused by SARS-CoV-2 type coronavirus.

Examples of coronavirus, e.g., COVID-19, related adverse events and/or symptoms include, without limitations, SARS, pneumonitis, fever, dry cough, fatigue, sputum production, loss of smell, loss of taste, mild or severe shortness of breath, hypoxia, muscle or joint pain, sore throat, headache, chills, nausea, vomiting, nasal congestion, diarrhea, severe bowel inflammation, abdominal pain, hemoptysis, pink eye, and a combination thereof.

In some embodiments, the instant disclosure may be directed to a method for treating a pulmonary adverse event associated with coronavirus (e.g., COVID-19) comprising administering to a patient experiencing a pulmonary adverse event a therapeutically effective amount of an ACE2 receptor modulator. The pulmonary adverse event may be SARS, pneumonitis or symptoms thereof.

The method may further comprise detecting and/or monitoring the pulmonary adverse event (prior to, during, or after administration of the ACE2 receptor modulator) with one or more of imaging, clinical exam, bronchoscopy, transbronchial biopsy, pulmonary function tests, CT, 6-minute walk test, resting $O_2$ saturation, electrocardiogram (EKG), eye exam, or a combination thereof.

In certain embodiments, the ACE2 receptor modulator comprises an ACE2 receptor inhibitor, an ACE2 receptor activator, or a combination thereof. The ACE2 receptor inhibitor is believed to bind to the ACE2 receptor and inhibit its interaction with a coronavirus spike protein, thereby inhibiting the coronavirus's entry into the cell. The ACE2 receptor activator is believed to interact with the ACE2 receptor, thereby deforming the ACE2 receptor in a manner that prevents the ACE2 receptor from interacting with a coronavirus spike protein, thereby inhibiting the coronavirus's entry into the cell.

The ACE2 receptor modulator can be permeable to the blood brain barrier such that a central effect is provided or impermeable to the blood brain barrier such that a central effect is not provided. In certain embodiments, the ACE2 receptor modulator can be partially permeable to the blood brain barrier such that a central effect is not provided.

In certain embodiments, suitable ACE2 receptor modulators include H1 receptor antagonists, H2 receptor antagonists, or a combination thereof.

Exemplary classes of suitable H1 receptor antagonists include, without limitations, ethylene diamines (e.g., mepyramine, chloropyramine, antazoline, tripelennamine), ethanolamines (e.g., diphenhydramine carbinoxiamine, doxylamine, orphanadrine, bromazine, clemastine, dimenhydrinate), alkylamines (pheniramine, chloropheniramine, dexchlorpheniramine, dexbrompheniramine, bromopheniramine, triprolidine, dimetindene), piperazines (cyclizine, chlorcyclizine, hydroxyzine, mecilizine), tricyclics and tetracyclics (promethazine, alimemazine, cyproheptadine), or a combination thereof.

In certain embodiments, suitable ACE2 receptor modulators include hydroxyzine, cetirizine, azelastine, fexofenadine, loratadine, diphenhydramine, mepiramine, chloropyramine, antazoline, tripeleneamine, carbinoxiamine, doxylamine, orphanadrine, bromazine, clemastine, dimenhydrinate, pheniramine, chloropheniramine, dexchlorpheniramine, dexbrompheniramine, bromopheniramine, triprolidine, dimetindene, cyclizine, chlorcyclizine, mecilizine, promethazine, alimemazine, cyproheptadine, olopatadine, ketotifen, famotidine, cimetidine, ranitidine, clemastine, desloratadine, rupatadine, carbinoxamine, triprolidine, astemizole, levocabastine, bepotasine, ebastine, nizatidine, roxatidine, lafutidine, niperotidine, benazepril, captopril, enalapril, fosinopril, lisinopril, moexipril, perindopril, quinapril, ramipril, trandolapril, pharmaceutically acceptable salts thereof, and combinations thereof.

In certain embodiments, suitable ACE2 receptor modulators include hydroxyzine, cetirizine, azelastine, diphenhydramine, benazepril, captopril, enalapril, fosinopril, lisinopril, moexipril, perindopril, quinapril, ramipril, trandolapril, pharmaceutically acceptable salts thereof, and combinations thereof.

In certain embodiments, suitable ACE2 receptor modulators include hydroxyzine, cetirizine, azelastine, diphenhydramine, pharmaceutically acceptable salts thereof, and combinations thereof.

Exemplary chemical structures of these ACE2 receptor modulators are depicted below.

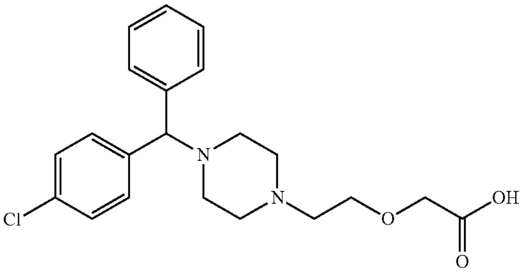
cetirizine
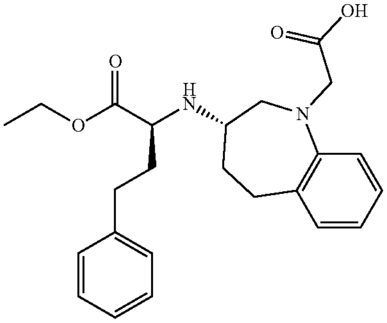
benazepril
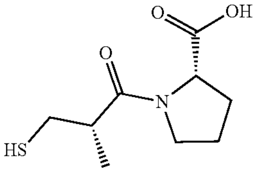
captopril
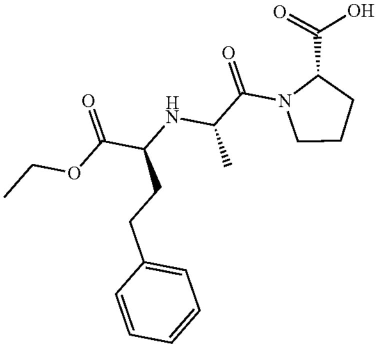
enalapril
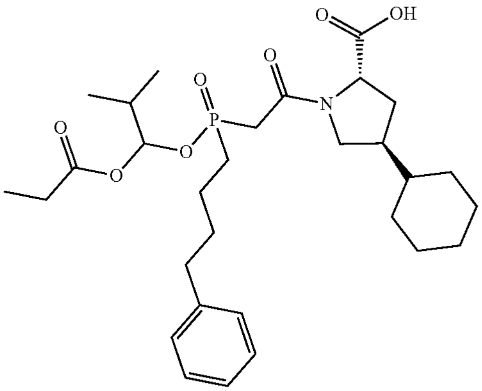
fosinopril
-continued
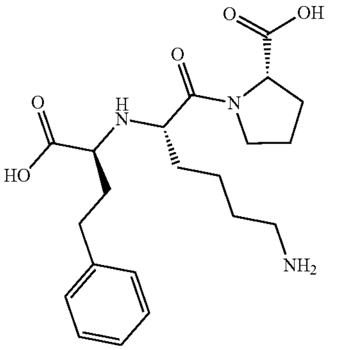
lisinopril
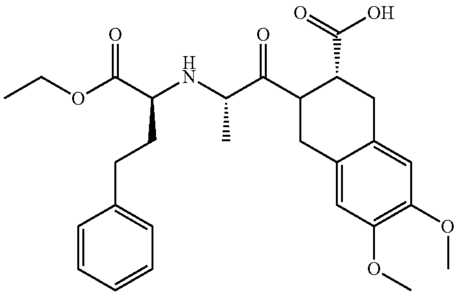
moexipril
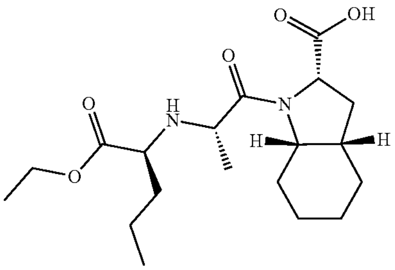
perindopril
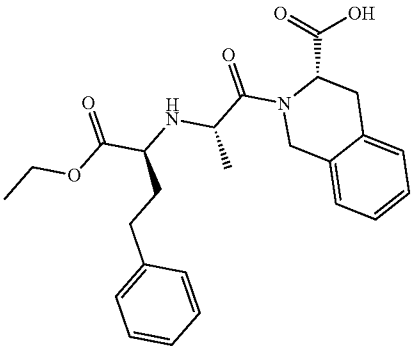
quinapril -continued
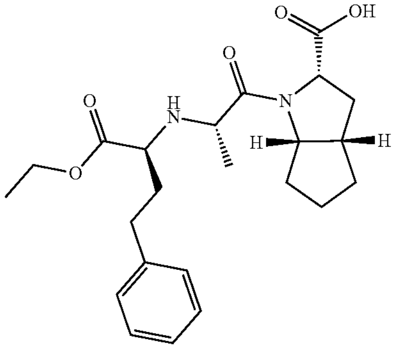
ramipril
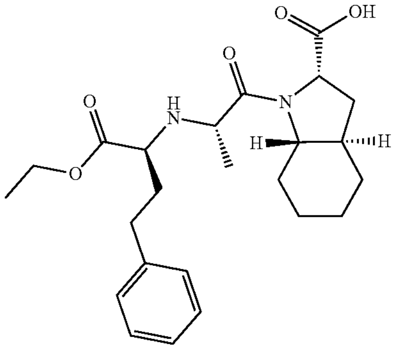
trandolapril
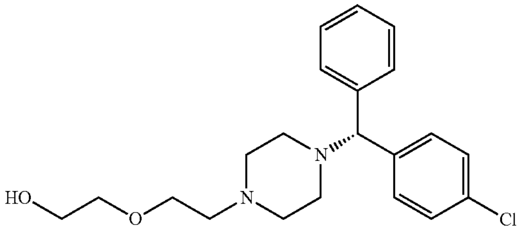
hydroxyzine
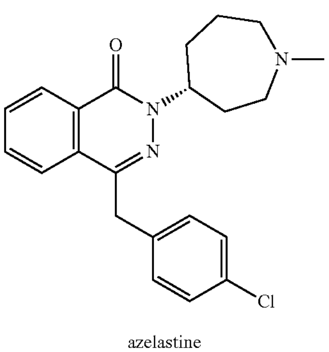
azelastine
-continued
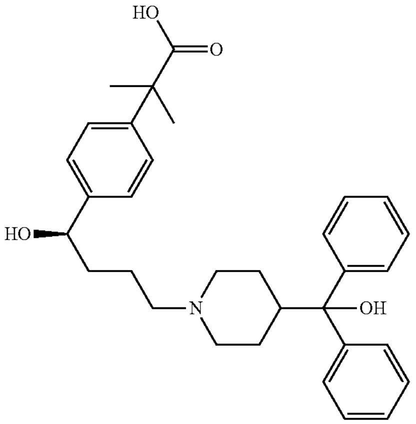
fexofenadine
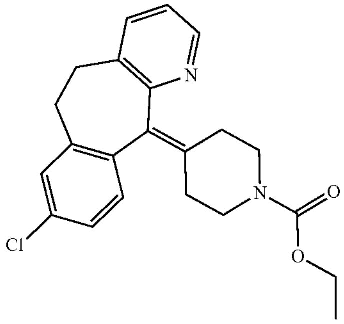
loratadine
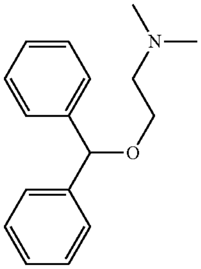
diphenhydramine
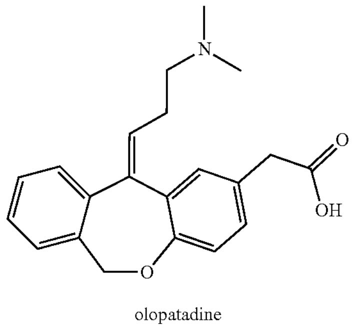
olopatadine -continued
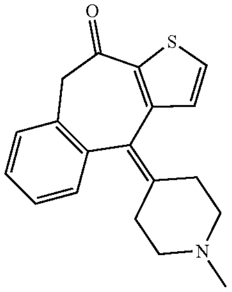
ketotifen
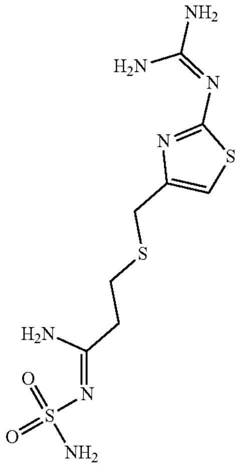
famotidine
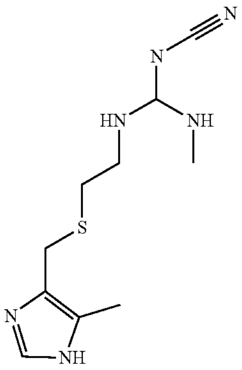
cimetidine
-continued
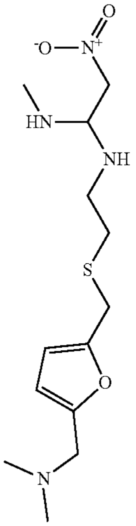
ranitidine
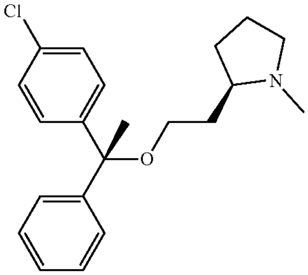
clemastine
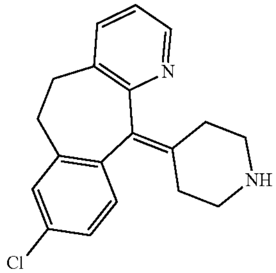
desloratadine
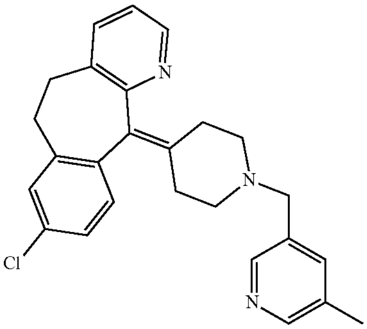
rupatadine -continued

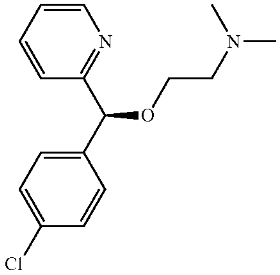

carbinoxamine

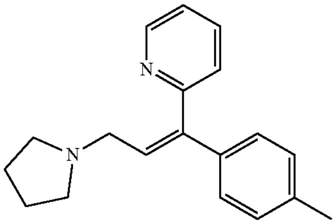

triprolidine

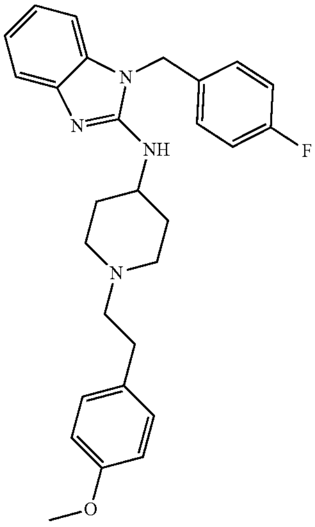

astemizole

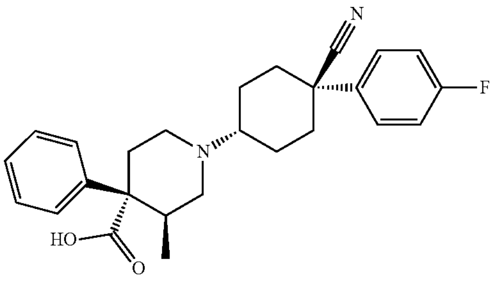

levocabastine

-continued

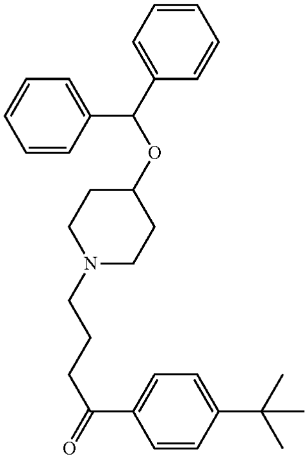

ebastine

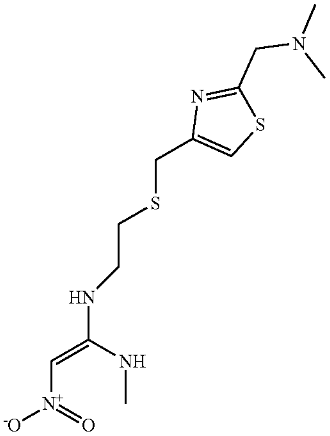

nizatidine

Suitable ACE2 receptor modulators may be available in a single-enantiomer form and/or as a racemic mixture.

For instance, cetirizine exists as an L-stereoisomer, referred to as levocetirizine, and as a D-stereoisomer, referred to as dextrocetirizine. The chemical structure of both isomers is depicted below.

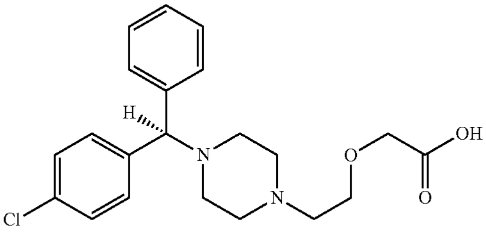

levocetirizine (L-stereoisomer)

-continued

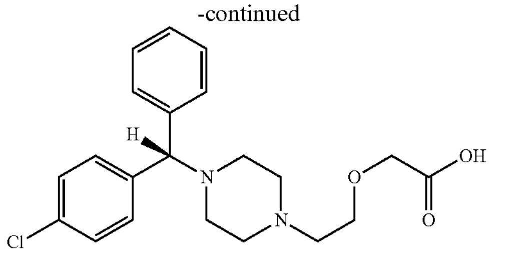

dextrocetirizine (D-stereoisomer)

In certain embodiments, the ACE2 receptor modulator includes levocetirizine (R enantiomer), dextrocetirizine (S enantiomer), pharmaceutically acceptable salts thereof, or a combination thereof (e.g., a racemic mixture of levocetirizine and dextrocetirizine).

In certain embodiments, the ACE2 receptor modulator includes a racemic mixture of levocitrizine and dextrocetirizine, wherein the racemic mixture includes more dextrocetirizine than levocitrizine. For instance, the racemic mixture, in embodiments, includes a weight ratio of dextrocetirizine to levocitrizine ranging from any of about 50:1, about 45:1, about 40:1, about 35:1, about 30:1, about 25:1, about 20:1, or about 15:1 to any of about 12:1, about 10:1, about 9:1, about 8:1, about 7:1, about 6:1, about 5:1, about 4:1, about 3:1, about 2:1, about 1.75:1, about 1.5:1, or about 1.25:1.

In one embodiment, the ACE2 receptor modulator includes dextrocetirizine and is substantially free of levocetirizine. The term "substantially free of levocetirizine" as used herein means that the racemic mixture contains a greater proportion of the d-isomer of cetirizine (dextrocetirizine) in relation to the l-isomer of cetirizine (levocetirizine). In certain embodiments, the term "substantially free of levocetirizine" as used herein means that the racemic mixture comprises at least 90% by weight of the d-isomer of cetirizine (dextrocetirizine) and 10% by weight or less of the l-isomer of cetirizine (levocetirizine). In other embodiments the term "substantially free of levocetirizine" means that the racemic mixture contains at least 99% by weight of the d-isomer of cetirizine (dextrocetirizine), and 1% or less of the l-isomer of cetirizine (levocetirizine). In yet other embodiments, the term "substantially free of levocetirizine" as used herein means that the racemic mixture contains greater than 99% by weight of the d-isomer of cetirizine (dextrocetirizine).

In certain embodiments, the ACE2 receptor includes the R enantiomer of azelastine, the S enantiomer of azelastine, pharmaceutically acceptable salts thereof, or a combination thereof (e.g., a racemic mixture of the R enantiomer and S enantiomer of azelastine).

In certain embodiments, the ACE2 receptor modulator exhibits a higher affinity for the ACE2 receptor than for the ACE1 receptor. Suitable ACE2 receptor modulators can exhibit an affinity for the ACE2 receptor, e.g., ranging from about 2 times to about 100 times, from about 5 times to about 90 times, from about 10 times to about 80 times, from about 15 times to about 70 times, from about 20 times to about 60 times, from about 25 times to about 50 times, from about 30 times to about 40 times, from about 2 times to about 10 times, from about 3 times to about 9 times, from about 4 times to about 8 times, from about 5 times to about 7 times, or from any of about 2, 3, 4, 5, 6, 7, 8, 9, 10, 15, 20, 25, 30, 35, 40, 45, 50, 60, 70, 80, 90, or 100 to about 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, or 1000 greater than its affinity for the ACE1 receptor.

Suitable routes of administration for the compositions and methods of the present invention can include, without limitations, oral, intravenous, nasal, inhalational, topical, buccal, rectal, pleural, peritoneal, vaginal, intramuscular, subcutaneous, transdermal, epidural, intratrachael, otic, intraocular, or intrathecal route.

In certain embodiments, the ACE2 receptor modulator is administered via a pulmonary route, such as via oral inhalative administration or intranasal administration.

Exemplary oral inhalative administration includes intratracheal instillation or intratracheal inhalation with an endotracheal tube.

Intratracheal instillation includes in embodiments administering a solution or suspension that includes the ACE2 receptor modulator to the pulmonary system by syringe.

In certain embodiments, intratracheal inhalation includes inhaling an aerosol that includes the ACE2 receptor modulator (e.g., via a metered dose inhaler). In other embodiments, intratracheal inhalation includes inhaling a nebulized solution that includes the ACE2 receptor modulator (e.g., via a jet nebulizer, an ultrasonic nebulizer, or a vibrating mesh nebulizer). In yet other embodiments, intratracheal inhalation includes inhaling a powder that includes the ACE2 modulator (e.g., via a dry powder inhaler).

In certain embodiments, the pharmaceutical composition may be administered via pulmonary administration at a flow rate of from any of about 1 lpm, 2 lpm, 4 lpm, 5 lpm, 7 lpm, or 10 lpm to any of about 12 lpm, 15 lpm, 17 lpm, 20 lpm or 25 lpm.

In certain embodiments, pharmaceutical compositions used in the present invention may be administered in a single daily dose, or the total daily dosage may be administered in divided doses of two, three or four times daily and may optionally be administered just before or with a meal (e.g., in a fed or fasted state). In certain methods of the present invention, the dosing regimen of the pharmaceutical composition is hourly, every two hours, every three hours, every four hours, every 5 hours, four times daily (once every 6 hours), three times daily (once every 8 hours), twice daily (once every 12 hours), once daily, once every 48 hours, once every 72 hours, once every 96 hours, once every 120 hours, once every 144 hours, or once every 168 hours. In certain methods of the present invention, the dosing may be via continuous intravenous infusion or nebulization.

In certain embodiments, each administration can be for at least 1 minute, at least 5 minutes at least 10 minutes, at least 15 minutes, at least 20 minutes, at least 30 minutes, at least 45 minutes, at least 1 hour, at least 2 hours, at least 4 hours, at least 6 hours, at least 8 hours, at least 12 hours, or at least 24 hours as a single treatment or according to the duration of treatment and dosing regimen disclosed herein.

The ACE2 receptor modulator can be used in the methods of the present invention in an amount, e.g., from any of about 0.01 mg, about 1 mg, about 5 mg, about 10 mg, about 25 mg, about 50 mg, about 75 mg, about 100 mg, about 150 mg, about 200 mg, or about 250 mg to any of about 300 mg, about 350 mg, about 400 mg, about 450 mg, about 500 mg, about 600 mg, about 700 mg, about 800 mg, about 900 mg, or about 1000 mg of active ingredient per day in a single or divided dose (e.g., twice, three or four times daily). In certain embodiments, the dose administered is high enough to effectively treat, minimize, prevent, or inhibit any of the coronavirus related adverse events described herein, yet low enough to minimize side effects that may otherwise be observed with higher doses.

In certain embodiments, the duration of the treatment with the pharmaceutical compositions described herein is (continuously or intermittently) over a time period, e.g., of up to 30 days, up to 25 days, up to 20 days, up to 15 days, up to 10 days, up to 7 days, up to 6 days, up to 5 days, up to 4 days, up to 3 days, up to 2 days (48 hours), or up to 1 day (24 hours). In certain embodiments, the pharmaceutical composition is administered over a duration that is long enough to effectively treat, minimize, prevent, or inhibit any of the coronavirus related adverse events described herein, yet short enough to minimize side effects that may otherwise be observed with chronic administration of the pharmaceutical composition.

In certain methods of the present invention, administering a pharmaceutical composition as disclosed herein to a patient experiencing a pulmonary adverse event according to an embodiment increases oxygen level in the blood by up to about 1%, up to about 2%, up to about 3%, up to about 4%, up to about 5%, up to about 6%, up to about 7%, up to about 8%, up to about 9%, up to about 10%, up to about 12%, up to about 14%, up to about 16%, up to about 18%, or up to about 20% compared to baseline. "Baseline" as used herein referring to the oxygen level in the blood of the patient experiencing said pulmonary adverse event prior to initiation of treatment with the pharmaceutical composition described herein. In other embodiments, the oxygen level in the blood is increased at least about 1%, at least about 2%, at least about 3%, at least about 4%, at least about 5%, at least about 6%, at least about 7%, at least about 8%, at least about 9%, at least about 10%, at least about 12%, at least about 14%, at least about 16%, at least about 18%, or at least about 20% compared to baseline.

In certain embodiments, the ACE2 receptor modulator can be administered along with additional active agents as part of a combined treatment regimen. In such combined treatment regimen, the ACE2 receptor modulator and any additional active agent can be administered at the same time. The agents can be combined in the same dosage form or be in separate dosage forms. When in separate dosage forms the agents can be administered by the same route of administration (e.g., pulmonary) or by different routes of administration (e.g., parenteral and pulmonary).

In certain embodiments, the ACE2 receptor inhibitor and the additional active agent can be administered simultaneously, sequentially, or concurrently. In certain embodiments, the two agents are administered sequentially such that there is an overlap of the therapeutic interval provided by each agent. With sequential administration, the agents are in separate dosage forms and can be administered by the same route of administration (e.g., pulmonary) or by different routes of administration (e.g., parenteral and pulmonary).

The term "simultaneously" as used herein means that a dose of one agent is administered at the same time as another agent, regardless of whether the agents are administered separately via the same or different routes of administration or in a single pharmaceutical composition or dosage form. For example, a dose of the ACE2 receptor modulator may be administered at the same time as a dose of an additional active agent.

The term "sequentially" as used herein means that a dose of one agent is administered first and thereafter a dose of another agent is administered second. For example, a dose of an ACE2 receptor modulator may be administered and thereafter a dose of an additional active agent may be administered. The subsequent administration of the additional active agent may be inside or outside the dosing interval of the ACE2 receptor modulator that was administered first.

The term "concurrent," as used herein, refers to an overlap in the therapeutic window of the ACE2 receptor modulator and the additional active agent. The two active agent(s) can be administered simultaneously, but simultaneous administration is not required.

Pharmaceutical Compositions

In certain embodiments, the present invention is directed to pharmaceutical compositions comprising a therapeutically effective amount of an angiotensin-converting enzyme 2 (ACE2) receptor modulator to reduce, prevent, treat, or ameliorate coronavirus and/or one or more of its related adverse events.

The pharmaceutical compositions described herein may include any of the ACE2 receptor modulators described hereinbefore and may reduce, prevent, treat, or ameliorate any of the coronaviruses and/or one or more of their related adverse events as described hereinbefore.

Pharmaceutical composition may be formulated in a manner suitable for administration by various routes including, without limitations, oral, intravenous, nasal, inhalational, topical, buccal, rectal, pleural, peritoneal, vaginal, intramuscular, subcutaneous, transdermal, epidural, intratrachael, otic, intraocular, or intrathecal.

In certain embodiments, the pharmaceutical compositions described herein may be formulated in a manner suitable for administration via the pulmonary route, such as via oral inhalative administration or intranasal administration, since it could offer several advantages over systemic administration. The advantages include, without limitations, direct delivery to the site of interest (i.e. lungs) and reduced side effects. For inhalation or intranasal administration, the ACE2 receptor modulator can be administered using a nebulizer, inhaler, atomizer, aerosolizer, mister, dry powder inhaler, metered dose inhaler, metered dose sprayer, metered dose mister, metered dose atomizer, or other suitable delivery device.

In certain embodiments, the pharmaceutical compositions described herein may be in a form of a solution, a suspension, an aerosol, or a dry powder. In one embodiment, the solution or suspension may be contained in a metered dose inhaler. In one embodiment, the powder may be contained in a dry powder inhaler.

In certain embodiments, the pharmaceutical composition comprises particles having a particle size ranging from any of about 0.1 μm, about 0.2 μm, about 0.3 μm, about 0.4 μm, about 0.5 μm, about 0.6 μm, about 0.7 μm, about 0.8 μm, about 0.9 μm, or about 1 μm to any of about 2 μm, about 3 μm, about 4 μm, about 5 μm, about 6 μm, about 7 μm, about 8 μm, about 9 μm, about 10 μm, or about 15 μm.

In certain embodiments, a single dose of the pharmaceutical composition may have a volume ranging from any of about 0.1 mL, about 0.2 mL, about 0.3 mL, about 0.4 mL, about 0.5 mL, about 0.6 mL, about 0.7 mL, about 0.8 mL, about 0.9 mL, or about 1 mL to any of about 1.5 mL, about 2 mL, about 2.5 mL, about 3.0 mL, about 3.5 mL, about 4.0 mL, about 4.5 mL, about 5.0 mL, about 7.5 mL, about 10 mL, about 15 mL, about 30 mL, about 60 ml, about 90 mL or about 120 mL.

In certain embodiments, the concentration of the ACE2 receptor modulator in the pharmaceutical composition may range from any of about 0.01 mg/mL, about 0.05 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.25 mg/mL, about 1.5 mg/mL, about 1.75 mg/mL, about 2.0 mg/mL, about 2.5 mg/mL, or about 3.0 mg/mL to any of about 4 mg/mL, about 4.5 mg/mL, about 5 mg/mL, about 5.5 mg/mL, about 6.0 mg/mL, about 6.5 mg/mL, about 7.0 mg/mL, about 7.5 mg/mL, about 8 mg/mL, about 8.5 mg/mL, about 9.0 mg/mL, about 9.5 mg/mL, about 10.0 mg/mL, about 50 mg/mL or about 100 mg/mL.

The pharmaceutical composition can comprise an ACE2 receptor modulator in an amount (w/w) from about 1% to about 99%, about 10% to about 90%, about 20% to about 80%, about 30% to about 70%, about 40% to about 60% or about 45% to about 55%.

Various excipients may be utilized to formulate pharmaceutical compositions suitable for a particular route of administration or to attain a particular release profile. The excipient can be in an amount (w/w) from about 1% to about 99%, about 10% to about 90%, about 20% to about 80%, about 30% to about 70%, about 40% to about 60% or about 45% to about 55%.

The pharmaceutically acceptable excipient may include, without limitations, solvents, suspension mediums, surfactants (e.g., dodecyl b-maltoside), dyes, perfumes, thickening agents, stabilizers, skin penetration enhancers, preservatives, antioxidants, other active agents (e.g., anesthetics or analgesics) and combinations thereof.

The pharmaceutical composition may optionally include one or more preservatives, e.g., methyl hydroxybenzoate, propyl hydroxybenzoate, chlorocresol, benzalkonium chlorides, and the like.

Other suitable excipients may include, for example, starch, glucose, lactose, mannitol, magnesium stearate, talc, cellulose, magnesium carbonate, sodium bicarbonate, citric acid, water, saline solution, aqueous dextrose, glycerol, alcohols (e.g., propylene glycol, phenoxyethanol, methanol, ethanol, isopropyl alcohol, and mixtures thereof) mineral oil, lanolin, gums of vegetable origin, polyalkylene glycols, and the like.

Surfactants useful in the compositions of the present invention include those selected from the group consisting of dodecyl b-maltoside, sarcosinates, dioctyl sodium sulfoscuccinate, pluronic F68, sodium lauryl sulfate, sorbitan monolaurate, lauryldimethylamineoxide, lauric-diethanolamide, PEG-Esters (polyethylene glycoldilaurate), coconut hydroxyethyl imidazoline, sodium sulfosuccinate ester of lauric MEA, sodium sulfosuccinate ester of ethoxylated lauryl alcohol, lauric-monoethanolamide, bis-(2-hydroxyethyl) cocoamine oxide, polyoxypropylene bases, coconut fatty acid, 2-sulfo-ester, sodium salt, N-coconut oil acyl-N-methyl taurine, sodium salt, lauroyl sarcosine, 30% sodium lauryl sarcosinate, sodium lauroyl sarcosinate, myristoyl sarcosine, oleoyl sarcosine, stearoyl sarcosine, polyoxyethelene 21 stearyl ether (0.1 BHA & 0.005% citric acid as preservatives), lauroamphoglycinate, lauroamphocarboxyglycinate, lauroamphocarboxypropinate, lauroamphocarboxyglycinate-sulfanate, sodium lauryl sulfate (66% lauryl, 27% myristyl, 71% cetyl), polyoxyethylene sorbitan monooleate, and mixtures thereof.

Some additional, exemplary, non-limiting excipients that may be used for certain dosage forms are described below.

In some embodiments, the pharmaceutical composition may be suitable for oral administration such as a pressed tablet, capsule (gelatin capsules, HPMC, hard shell, soft shell, or any other suitable capsule), enteric coated tablet, osmotic release tablet or capsule, unique combination of excipients, a chewable gum, lozenge, candy, or an edible form.

In some embodiments, the pharmaceutical composition may be formulated in a manner suitable for parenteral administration, such as a solution, a suspension (e.g., an aqueous suspension), a dispersion, an emulsion, or a powder.

In some embodiments, the pharmaceutical composition may be formulated in a manner suitable for topical administration, such as solutions, ointments, creams, suspensions, lotions, powders, pastes, gels, sprays, aerosols, or oils, a patch, or a dressing.

In certain embodiments, the dosage forms disclosed herein may be formulated as a matrix encompassing the active agent(s), optionally along with one or more pharmaceutically acceptable excipients. In other embodiments, the dosage forms disclosed herein may be formulated in a layered manner where the active agent(s), optionally with one or more pharmaceutically acceptable excipients, may be in one or more layers, and one or more additional pharmaceutically acceptable excipient(s) and/or one or more additional active agent(s) may be in another layer. In yet other embodiments, the dosage forms disclosed herein may be formulated as particles (e.g., microspheres, micelles, granules, extrudates). The particles themselves could be dispersed in a matrix and/or contain layers.

The pharmaceutical compositions of the invention additionally include a pharmaceutically acceptable excipient. The term "pharmaceutically acceptable excipient" refers to any inert ingredient in a composition is combined with an active agent in a formulation. A pharmaceutically acceptable excipient can include, but is not limited to, carbohydrates (such as glucose, sucrose, dextrans, maltose, galactose, rhamnose, lactose, dextrose, sugar alcohols (e.g., mannitol, xylitol, sorbitol), and combinations thereof), antioxidants (such as ascorbic acid or glutathione), chelating agents, low-molecular weight proteins, high-molecular weight polymers, gel-forming agents or other stabilizers and additives, solvents, diluents, or other liquid vehicle, adjuvants, dispersion or suspension aids or surfactants, surface active agents, isotonic agents, wetting agents, thickening (also viscosity enhancing agent) or emulsifying agents, preservatives, binders, lubricants, disintegrants, osmotic agents, pore formers, hygroscopic polymer, hydrophilic polymers, rate-controlling polymer, materials for forming semi-permeable layers, biocompatible polymers, pH adjusting agents, sweeteners, flavorants, colorants, releasing agents, coating agents, perfuming agents, preservatives, antioxidants, stabilizers, lubricants, and auxiliary agents as suited to the particular dosage form desired. Remington's Pharmaceutical Sciences, 18th Edition, A. R. Gennaro (Mack Publishing Co., Easton, Pa., 1990) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this invention.

Some examples of materials which can serve as pharmaceutically acceptable excipients include, but are not limited to:

Solvents and/or diluents and/or liquid vehicles such as, without limitations, ethyl acetate, triacetin, dimethyl sulfoxide also known as "DMSO", propylene carbonate, N-methylpyrrolidone (NMP), ethyl alcohol, ethylmethylketone, hexane, toluene, benzyl alcohol, glycofurol, alpha-tocopherol, Miglyol 810, isopropyl alcohol, diethyl phthalate, polyethylene glycol 400 (PEG 400), triethyl citrate, benzyl benzoate, sucrose acetate isobutyrate (SA1 B), cellulose acetate butyrate (CAB) 381-20, 1,3-butanediol, Ringer's solution, water and oils (including those of petroleum, animal, vegetable or synthetic origin, such as cocoa butter, suppository waxes, peanut oil, cottonseed oil, safflower oil, olive oil, castor oil, corn oil, soybean oil, mineral oil, sesame oil, polyoxyethylated versions thereof, and the like), saline, glycerol solution, gum acacia, gelatin, starch paste (e.g., corn starch and potato starch), talc, keratin, colloidal silica, urea, phospholipon 90 G (e.g., phosphatidylchloine stabilized with 0.1 wt % ascorbyl palmitate, optionally including up to 4.0 wt % lysophosphatidylcholine and/or up to 0.3 wt % tocopherol), sodium desoxycholate, the like, and combinations thereof;

Dispersion or suspension aid or surfactants, such as, without limitations, Tweens, other similar polymeric delivery matrices, synthetic mono- or diglycerides, fatty acids, such as, but not limited to, oleic acid and its glyceride derivatives, carboxymethylcellulose, Spans, and combinations thereof.

Thickening (also viscosity enhancing agent(s)) or emulsifying agents, such as, without limitations, caprylic/capric triglyceride (Migliol 810), isopropyl myristate (IPM), ethyl oleate, triethyl citrate, dimethyl phthalate, benzyl benzoate, various grades of polyethylene oxide, and combinations thereof;

Preservatives, such as, without limitations, phenol, ascorbic acid, and combinations thereof;

Binders, such as, without limitations, hydroxyalkylcellulose, a hydroxyalkylalkylcellulose, a polyvinylpyrrolidone, and combinations thereof;

Disintegrants, such as, without limitations, croscarmellose sodium, crospovidone, sodium alginate, similar excipients, and combinations thereof;

Osmotic agents, such as, without limitations, sorbitol, mannitol, sodium chloride, other salts, and combinations thereof.

Hygroscopic polymer, such as, without limitations, polyethylene oxide (e.g., Polyox® with MWs from 4,000,000 to 10,000,000), cellulose hydroxymethyl cellulose, hydroxyethyl-cellulose, crosslinked polyacrylic acids, xanthum gum, and combinations thereof;

Rate-controlling polymer, such as, without limitations, polymeric acrylate, methacrylate lacquer or mixtures thereof, polymeric acrylate lacquer, methacrylate lacquer, an acrylic resin including a copolymer of acrylic and methacrylic acid esters or an ammonium methacrylate lacquer with a plasticizer, and combinations thereof.

Biocompatible polymers, such as, without limitations, poly(hydroxyl acids), polyanhydrides, polyorthoesters, polyamides, polycarbonates, polyelkylenes, polyelkylene glycols, polyalkylene oxides, polyalkylene terepthalates, polyvinyl alcohols, polyvinyl ethers, polyvinyl esters, polyvinyl halides, polyvinylpyrrolidone, polysiloxanes, polyvinyl alcohols), poly (vinyl acetate), polystyrene, polyurethanes and co-polymers thereof, synthetic celluloses, polyacrylic acids, poly(butyric acid), poly(valeric acid), and poly(lactide-co-caprolactone), ethylene vinyl acetate, copolymers and blends thereof; Materials for forming semi-permeable layers, such as, without limitations, cellulosic polymers such as cellulose acetate, cellulose acylate, cellulose diacylate, cellulose triacylate, cellulose diacetate, cellulose triacetate or any mixtures thereof; ethylene vinyl acetate copolymers, polyethylene, copolymers of ethylene, polyolefins including ethylene oxide copolymers (e.g., Engage®-Dupont Dow Elastomers), polyamides, cellulosic materials, polyurethanes, polyether blocked amides, copolymers (e.g., PEBAX®, cellulosic acetate butyrate and polyvinyl acetate), and combinations thereof; pH adjusting agents, such as, without limitations, acids (e.g., hydrochloric acid, citric acid), bases (e.g., sodium hydroxide), or buffers (e.g., magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate) to enhance the stability of the formulated compound or its delivery form; auxiliary agents, such, without limitations, malt, rice, flour, chalk, silica gel, sodium stearate, glycerol monostearate, talc, dried skim milk, propylene glycol, ethanol, ion exchangers, alumina, aluminum stearate, lecithin, self-emulsifying drug delivery systems (SEDDS) such as d-E-tocopherol polyethylene-glycol 1000 succinate, serum proteins such as human serum albumin, buffer substances such as phosphates, glycine, sorbic acid, potassium sorbate, partial glyceride mixtures of saturated vegetable fatty acids, water, salts; or electrolytes, such as protamine sulfate, disodium hydrogen phosphate, potassium hydrogen phosphate, zinc salts, ethyl laurate, colloidal silica, magnesium trisilicate, polyvinyl pyrrolidone, cellulose-based substances (e.g., sodium carboxymethyl cellulose, ethyl cellulose and cellulose acetate), agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine, powdered tragacanth, hydrophobic materials such as one or more waxes, fatty alcohols and/or fatty acid esters, polyethylene glycol, sodium carboxmethylcellulose, polyacrylates, waxes, polyethylene-polyoxypropylene-block polymers, polyethylene glycol and wool fat. Cyclodextrins such as alpha, beta and gamma-cyclodextrin, or chemically modified derivatives such as hydroxyalkylcyclodextrins, including 2- and 3-hydroxypropyl-beta cyclodextrins, or other solubilized derivatives may also be used to enhance delivery of compound(s) of the formulations disclosed herein that can be used in the methods of the invention.

EXAMPLES

The following examples and/or studies are set forth to assist in understanding the invention and should not be construed as specifically limiting the invention described and claimed herein. Such variations of the invention, including the substitution of any or all equivalents now known or later developed, which would be within the purview of those skilled in the art, and changes in formulation or minor changes in therapeutic design, are to be considered to fall within the scope of the invention incorporated herein.

Example 1

Medication Use in COVID-19 Positive and Negative Patients

Methods

The primary objective of this study was to determine whether medications taken prior to infection with SARS-CoV-2 influence the risk of infection. The primary hypothesis was that antihistamines (H1 receptor inhibitors) individually, and when grouped as a class, provide protection from COVID-19 when taken on a routine basis for other indications such as allergies, sedation, etc. The secondary hypothesis was that other medications that can affect the histamine receptors (e.g. H2) may also offer protection. These include famotidine (Pepcid), nizatidine (Axid), and cimetidine (Tagamet).

Data was collected on demographics (gender, age, race) as well as comorbidities. Cases and controls were matched based on propensity scores (probability of taking antihistamines) estimated on the basis of demographics and comorbidities. Descriptive statistics for all study variables (means and standard deviations or medians and interquartile ranges for continuous variables, frequencies and percentages for categorical variables) were presented for both the original sample and the sample that remains after matching. Based on the matched sample, a chi-square or Fisher Exact test was performed to assess if there were differences in SARS-CoV-2 infection rates between antihistamine use. If covariate balance is not achieved, odds ratios from a logistic regression that controls for the unbalanced covariates was also presented. The analysis was repeated considering use of either H1 or H2 histamines, H1 use only, H2 use only and by individual drugs.

All variables were examined for evidence of miscodings and skew. Continuous variables demonstrating large skew were appropriately transformed. Missing data was also examined. If any variable had more than 5% missing, k-nearest neighbor imputation was used. Statistical significance was defined as $p<0.05$. All statistical analysis was performed in R Version 4.0.3.

Results

The original dataset consisted of 4,783 records of patients who were hospitalized between Jan. 1, 2020 and Dec. 30, 2020. N=38 patients under the age of 18 and were excluded, and one patient with a hospitalization date before Jan. 1, 2020 was dropped. There were 432 patients with multiple records, 91 of which had at least one positive test for SARS-CoV-2. For patients with multiple records that never tested positive for COVID, only the earliest record was used. For patients with multiple records that had at least one positive test, only the earliest record with a positive test was used. After these exclusions, the total sample included in the analysis was N=4,181 patients. There was no evidence of miscoding or skewness of the variables considered. Only PRISM score had a small amount of missingness (2.5%). K-Nearest neighbor imputation was used to impute the missingness in the PRISM variable.

Any Antihistamine Use (H1 or H2)

Demographics and comorbidities of the total sample by any antihistamine use (H1 or H2) are presented in Table 1. Several variables including gender, PRISM score, hypertension, asthma, COPD, CAD, and allergies were unbalanced between the antihistamine groups, with those using antihistamines (H1 or H2) having higher rates of comorbidities.

TABLE 1

Descriptive Statistics of Total Sample (N = 4,181) by Any Antihistamine Use (H1 or H2)

| Variable | Label | Antihistamine Use (N = 1062) | No Antihistamine Use (N = 3119) | p-value |
|---|---|---|---|---|
| Age (Years) | | 64.94 (17) | 64.32 (18.38) | 0.338 |
| Gender | | | | <0.001 |
| | Female | 614 (57.82%) | 1568 (50.27%) | |
| | Male | 448 (42.18%) | 1551 (49.73%) | |
| Race | | | | 0.728 |
| | African American | 189 (17.8%) | 575 (18.44%) | |
| | Am Indian/Alaskan Native | 4 (0.38%) | 7 (0.22%) | |
| | Asian | 12 (1.13%) | 44 (1.41%) | |
| | Hawaiian/Pac Islander | 0 (0%) | 3 (0.1%) | |
| | Multiracial | 4 (0.38%) | 9 (0.29%) | |
| | Unknown | 30 (2.82%) | 110 (3.53%) | |
| | White | 823 (77.5%) | 2371 (76.02%) | |
| Ethnicity: Hispanic/Latino | | 18 (1.69%) | 65 (2.08%) | 0.511 |
| PRISM Score | | 2.66 (1.16) | 2.81 (1.17) | <0.001 |
| Hypertension | | 797 (75.05%) | 2104 (67.46%) | <0.001 |
| Diabetes | | 432 (40.68%) | 1163 (37.29%) | 0.054 |
| Asthma | | 168 (15.82%) | 255 (8.18%) | <0.001 |
| COPD | | 339 (31.92%) | 737 (23.63%) | <0.001 |
| Obesity | | 216 (20.34%) | 555 (17.79%) | 0.072 |
| CAD | | 381 (35.88%) | 1003 (32.16%) | 0.029 |
| Allergies | | 25 (2.35%) | 25 (0.8%) | <0.001 |

After nearest-neighbor propensity score matching, the total sample was reduced to N=2,114 patients, with N=1,058 matched patients in each study group. The any antihistamine study groups showed relatively similar distributions (FIG. 1). Table 2 shows that after matching, the study groups were balanced and had no significant differences in any of the demographic and comorbidities.

TABLE 2

Descriptive Statistics of PS-Matched Sample (N = 2,114) by Any Antihistamine Use Cohorts (H1 or H2)

| Variable | Label | Antihistamine Use (N = 1058) | No Antihistamine Use (N = 1058) | p-value |
|---|---|---|---|---|
| Age (Years) | | 64.92 (17.02) | 64.99 (17.58) | 0.93 |
| Gender | | | | 0.269 |

TABLE 2-continued

| Descriptive Statistics of PS-Matched Sample (N = 2,114) by Any Antihistamine Use Cohorts (H1 or H2) | | | | |
|---|---|---|---|---|
| Variable | Label | Antihistamine Use (N = 1058) | No Antihistamine Use (N = 1058) | p-value |
| | Female | 610 (57.66%) | 636 (60.11%) | |
| | Male | 448 (42.34%) | 422 (39.89%) | |
| Race | | | | 0.896 |
| | African American | 187 (17.67%) | 185 (17.49%) | |
| | Am Indian/Alaskan Native | 3 (0.28%) | 1 (0.09%) | |
| | Asian | 12 (1.13%) | 11 (1.04%) | |
| | Multiracial | 4 (0.38%) | 3 (0.28%) | |
| | Unknown | 30 (2.84%) | 25 (2.36%) | |
| | White | 822 (77.69%) | 833 (78.73%) | |
| Ethnicity: Hispanic/Latino | | 18 (1.7%) | 18 (1.7%) | >0.999 |
| PRISM Score | | 2.67 (1.16) | 2.67 (1.17) | 0.867 |
| Hypertension | | 794 (75.05%) | 795 (75.14%) | >0.999 |
| Diabetes | | 430 (40.64%) | 421 (39.79%) | 0.723 |
| Asthma | | 164 (15.5%) | 159 (15.03%) | 0.809 |
| COPD | | 337 (31.85%) | 328 (31%) | 0.708 |
| Obesity | | 214 (20.23%) | 211 (19.94%) | 0.914 |
| CAD | | 381 (36.01%) | 376 (35.54%) | 0.856 |
| Allergies | | 22 (2.08%) | 20 (1.89%) | 0.876 |

Results for the primary outcome of SARS-CoV-2 infection rates between the matched treatment groups of any antihistamine use (H1 or H2) and no antihistamine use are shown in Table 3. After matching patients on demographics and comorbidities, there is not a significant difference in infection rates between the two groups (18.71% vs 20.04%, p-value=0.475). These results are confirmed in the multivariable logistic regression model results shown in Table 4 (OR=0.987, p-value=0.425).

TABLE 3

| Positive COVID Test Result by Any Antihistamine Use (H1 or H2) - PS-Matched Sample (N = 2,114) | | | |
|---|---|---|---|
| Variable | Antihistamine Use (N = 1058) | No Antihistamine Use (N = 1058) | p-value |
| SARS-CoV-2 Positive Test Result | 198 (18.71%) | 212 (20.04%) | 0.475 |

TABLE 4

| Multiple Logistic Regression Model for SARS-CoV-2 Infection - Any Antihistamine Use (H1 or H2) | | | |
|---|---|---|---|
| Covariate | Odds Ratio | 95% CI | p-value |
| Antihistamine Use (H1 or H2) | 0.987 | (0.955, 1.02) | 0.425 |
| Age | 1.002 | (1, 1.003) | 0.02 |
| Gender (Male) | 0.997 | (0.963, 1.032) | 0.866 |
| Race (African American) | 1.117 | (1.068, 1.168) | <0.001 |
| Race (Asian) | 1.241 | (1.058, 1.455) | 0.008 |
| Race (Am Indian/Alaskan Native) | 1.073 | (0.735, 1.569) | 0.714 |
| Race (Multiracial)) | 0.863 | (0.645, 1.154) | 0.319 |
| Race (Unknown) | 1.131 | (1.019, 1.255) | 0.021 |
| Ethnicity (Hispanic/Latino) | 1.138 | (1.001, 1.295) | 0.049 |
| Hypertension | 0.978 | (0.934, 1.024) | 0.344 |
| Diabetes | 1.048 | (1.011, 1.086) | 0.01 |
| Asthma | 0.970 | (0.925, 1.017) | 0.204 |
| COPD | 0.903 | (0.87, 0.937) | <0.001 |
| Obesity | 1.060 | (1.016, 1.107) | 0.008 |

TABLE 4-continued

| Multiple Logistic Regression Model for SARS-CoV-2 Infection - Any Antihistamine Use (H1 or H2) | | | |
|---|---|---|---|
| Covariate | Odds Ratio | 95% CI | p-value |
| CAD | 0.925 | (0.891, 0.961) | <0.001 |
| Allergies | 0.941 | (0.836, 1.061) | 0.321 |
| PRISM Score | 0.971 | (0.953, 0.988) | 0.001 |

Note:
White was the reference group for race.

Of the patients who tested positive in the PS-matched sample of any antihistamine (H1 or H2) users, there was not a significant difference in ICU admission rates (p-value=0.42, Appendix Table 5) or ICU length of stay (p-value=0.211).

TABLE 5

| ICU Admission and LOS of SARS-CoV-2 Positive Patients by Drug Use (any antihistamine, H1 or H2, users) - PS | | | | |
|---|---|---|---|---|
| Drug Type | Variable | Drug Use | No Drug Use | P Value |
| H1 or H2 | | N = 197 | N = 222 | |
| | ICU Admission | 36 (18.27%) | 33 (14.86%) | 0.42 |
| | ICU LOS | 11.64 (14.24) | 16.42 (17.18) | 0.211 |

Antihistamine Use (H1 Only)

Demographics and comorbidities of the total sample by H1 antihistamine use are presented in Table 6. Several variables including gender, hypertension, asthma, COPD, obesity, and allergies were unbalanced between the H1 antihistamine groups, with those using H1 antihistamines having higher rates of comorbidities.

TABLE 6

Descriptive Statistics of Total Sample (N = 4,181) by Antihistamine Use (H1 only)

| Variable | Label | H1 Antihistamine Use (N = 702) | No H1 Antihistamine Use (N = 3479) | p-value |
|---|---|---|---|---|
| Age (Years) | | 65.15 (16.73) | 64.34 (18.29) | 0.281 |
| Gender | | | | <0.001 |
| | Female | 421 (59.97%) | 1761 (50.62%) | |
| | Male | 281 (40.03%) | 1718 (49.38%) | |
| Race | | | | 0.108 |
| | African American | 128 (18.23%) | 636 (18.28%) | |
| | Am Indian/Alaskan Native | 3 (0.43%) | 8 (0.23%) | |
| | Asian | 9 (1.28%) | 47 (1.35%) | |
| | Hawaiian/Pac Islander | 0 (0%) | 3 (0.09%) | |
| | Multiracial | 3 (0.43%) | 10 (0.29%) | |
| | Unknown | 12 (1.71%) | 128 (3.68%) | |
| | White | 547 (77.92%) | 2647 (76.09%) | |
| Ethnicity: Hispanic/Latino | | 12 (1.71%) | 71 (2.04%) | 0.67 |
| PRISM Score | | 2.7 (1.17) | 2.79 (1.17) | 0.068 |
| Hypertension | | 523 (74.5%) | 2378 (68.35%) | 0.001 |
| Diabetes | | 290 (41.31%) | 1305 (37.51%) | 0.065 |
| Asthma | | 136 (19.37%) | 287 (8.25%) | <0.001 |
| COPD | | 230 (32.76%) | 846 (24.32%) | <0.001 |
| Obesity | | 154 (21.94%) | 617 (17.73%) | 0.01 |
| CAD | | 246 (35.04%) | 1138 (32.71%) | 0.249 |
| Allergies | | 17 (2.42%) | 33 (0.95%) | 0.002 |

Figure 2:
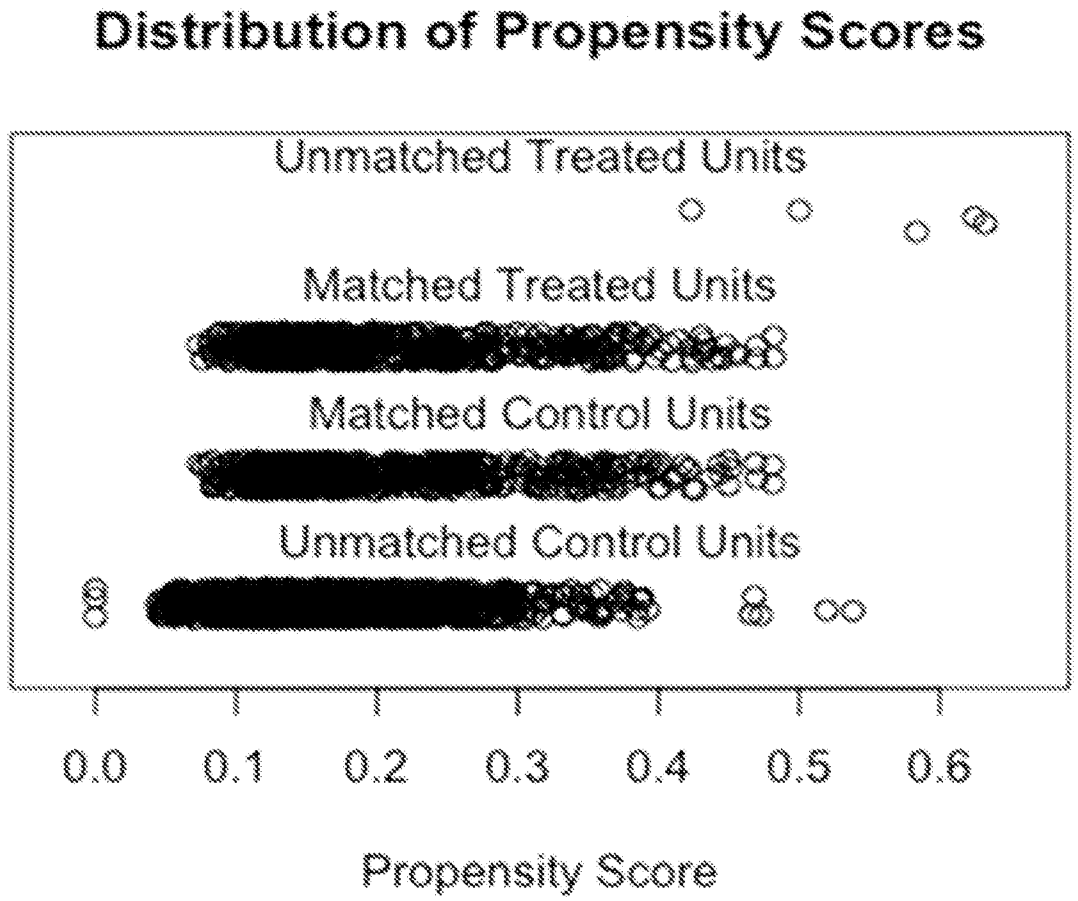
FIG. 2 illustrates distribution of propensity scores in the matched H1 antihistamine groups.

After nearest-neighbor propensity score matching, the total sample was reduced to N=1,398 patients, with N=697 matched patients in each study group. The H1 antihistamine study groups showed relatively similar distributions (FIG. 2). Table 7 shows that after matching, the study groups were balanced and had no significant differences in any of the demographic and comorbidities.

TABLE 7

Descriptive Statistics of PS-Matched Sample (N = 1,398) by Antihistamine Use Cohorts (H1 only)

| Variable | Label | H1 Antihistamine Use (N = 697) | No H1 Antihistamine Use (N = 697) | p-value |
|---|---|---|---|---|
| Age (Years) | | 65.17 (16.74) | 65.41 (17.83) | 0.796 |
| Gender | | | | 0.446 |
| | Female | 416 (59.68%) | 401 (57.53%) | |
| | Male | 281 (40.32%) | 296 (42.47%) | |
| Race | | | | 0.323 |
| | African American | 126 (18.08%) | 123 (17.65%) | |
| | Am Indian/Alaskan Native | 2 (0.29%) | 2 (0.29%) | |
| | Asian | 9 (1.29%) | 6 (0.86%) | |
| | Multiracial | 3 (0.43%) | 1 (0.14%) | |
| | Unknown | 12 (1.72%) | 4 (0.57%) | |
| | White | 545 (78.19%) | 561 (80.49%) | |
| Ethnicity: Hispanic/Latino | | 12 (1.72%) | 7 (1%) | 0.355 |
| PRISM Score | | 2.7 (1.17) | 2.72 (1.13) | 0.852 |
| Hypertension | | 519 (74.46%) | 516 (74.03%) | 0.903 |
| Diabetes | | 286 (41.03%) | 293 (42.04%) | 0.744 |
| Asthma | | 131 (18.79%) | 134 (19.23%) | 0.891 |
| COPD | | 227 (32.57%) | 226 (32.42%) | >0.999 |
| Obesity | | 150 (21.52%) | 152 (21.81%) | 0.948 |
| CAD | | 245 (35.15%) | 234 (33.57%) | 0.573 |
| Allergies | | 15 (2.15%) | 13 (1.87%) | 0.849 |

Results for the primary outcome of SARS-CoV-2 infection rates between the matched treatment groups of H1 antihistamine use and no H1 antihistamine use are shown in Table 8. After matching patients on demographics and comorbidities, there was not a significant difference in infection rates between the two groups (17.65% vs 20.09%, p-value=0.273). These results were confirmed in the multivariable logistic regression model results shown in Table 9 (OR=0.975, p-value=0.222).

TABLE 8

Positive COVID Test Result by Antihistamine Use (H1 only) - PS-Matched Sample (N = 1,398)

| Variable | H1 Antihistamine Use (N = 697) | No H1 Antihistamine Use (N = 697) | p-value |
|---|---|---|---|
| SARS-CoV-2 Positive Test Result | 123 (17.65%) | 140 (20.09%) | 0.273 |

TABLE 9

Multiple Logistic Regression Model for SARS-CoV-2 Infection - Antihistamine Use (H1 only)

| Covariate | Odds Ratio | 95% CI | p-value |
|---|---|---|---|
| Antihistamine Use (H1 only) | 0.975 | (0.937, 1.015) | 0.222 |
| Age | 1.002 | (1.001, 1.004) | 0.006 |
| Gender (Male) | 0.997 | (0.955, 1.04) | 0.877 |
| Race (African American) | 1.110 | (1.051, 1.171) | <0.001 |
| Race (Asian) | 1.007 | (0.827, 1.226) | 0.943 |
| Race (Am Indian/Alaskan Native) | 1.092 | (0.748, 1.593) | 0.649 |
| Race (Multiracial) | 0.858 | (0.586, 1.256) | 0.43 |
| Race (Unknown) | 1.249 | (1.033, 1.511) | 0.022 |
| Ethnicity (Hispanic/Latino) | 1.027 | (0.861, 1.224) | 0.769 |
| Hypertension | 0.989 | (0.936, 1.046) | 0.707 |
| Diabetes | 1.043 | (0.998, 1.09) | 0.062 |
| Asthma | 0.955 | (0.905, 1.008) | 0.093 |
| COPD | 0.905 | (0.865, 0.947) | <0.001 |
| Obesity | 1.057 | (1.003, 1.113) | 0.037 |
| CAD | 0.932 | (0.89, 0.977) | 0.004 |

TABLE 9-continued

Multiple Logistic Regression Model for SARS-CoV-2 Infection - Antihistamine Use (H1 only)

| Covariate | Odds Ratio | 95% CI | p-value |
|---|---|---|---|
| Allergies | 0.934 | (0.808, 1.079) | 0.352 |
| PRISM Score | 0.972 | (0.95, 0.994) | 0.012 |

Note:
White was the reference group for race.

Of the patients who tested positive in the PS-matched sample of H1 antihistamine users, there was not a significant difference in ICU admission rates (p-value=0.679, Table 10) or ICU length of stay (p-value=0.119).

TABLE 10

ICU Admission and LOS of SARS-CoV-2 Positive Patients by Drug Use (H1 only users) - PS

| Drug Type | Variable | Drug Use | No Drug Use | P Value |
|---|---|---|---|---|
| H1 Only | | N = 124 | N = 133 | |
| | ICU Admission | 21 (16.94%) | 19 (14.29%) | 0.679 |
| | ICU LOS | 17.52 (18.06) | 10.26 (8.67) | 0.119 |

Antihistamine Use (H2 Only)

Demographics and comorbidities of the total sample by H2 antihistamine use are presented in Table 11. Several variables including gender, PRISM score, hypertension, and COPD are unbalanced between the H2 antihistamine groups, with those using H2 antihistamines having higher rates of comorbidities.

TABLE 11

Descriptive Statistics of Total Sample (N = 4,181) by Antihistamine Use (H2 only)

| Variable | Label | H2 Antihistamine Use (N = 468) | No H2 Antihistamine Use (N = 3713) | p-value |
|---|---|---|---|---|
| Age (Years) | | 64.1 (17.34) | 64.53 (18.12) | 0.633 |
| Gender | | | | 0.006 |
| | Female | 273 (58.33%) | 1909 (51.41%) | |
| | Male | 195 (41.67%) | 1804 (48.59%) | |
| Race | | | | 0.754 |
| | African American | 80 (17.09%) | 684 (18.42%) | |
| | Am Indian/Alaskan Native | 2 (0.43%) | 9 (0.24%) | |
| | Asian | 4 (0.85%) | 52 (1.4%) | |
| | Hawaiian/Pac Islander | 0 (0%) | 3 (0.08%) | |
| | Multiracial | 1 (0.21%) | 12 (0.32%) | |
| | Unknown | 19 (4.06%) | 121 (3.26%) | |
| | White | 362 (77.35%) | 2832 (76.27%) | |
| Ethnicity: Hispanic/Latino | | 7 (1.5%) | 76 (2.05%) | 0.529 |
| PRISM Score | | 2.62 (1.16) | 2.79 (1.17) | 0.002 |
| Hypertension | | 353 (75.43%) | 2548 (68.62%) | 0.003 |
| Diabetes | | 196 (41.88%) | 1399 (37.68%) | 0.087 |
| Asthma | | 59 (12.61%) | 364 (9.8%) | 0.07 |
| COPD | | 147 (31.41%) | 929 (25.02%) | 0.003 |
| Obesity | | 83 (17.74%) | 688 (18.53%) | 0.723 |
| CAD | | 170 (36.32%) | 1214 (32.7%) | 0.129 |
| Allergies | | 8 (1.71%) | 42 (1.13%) | 0.39 |

Figure 3:
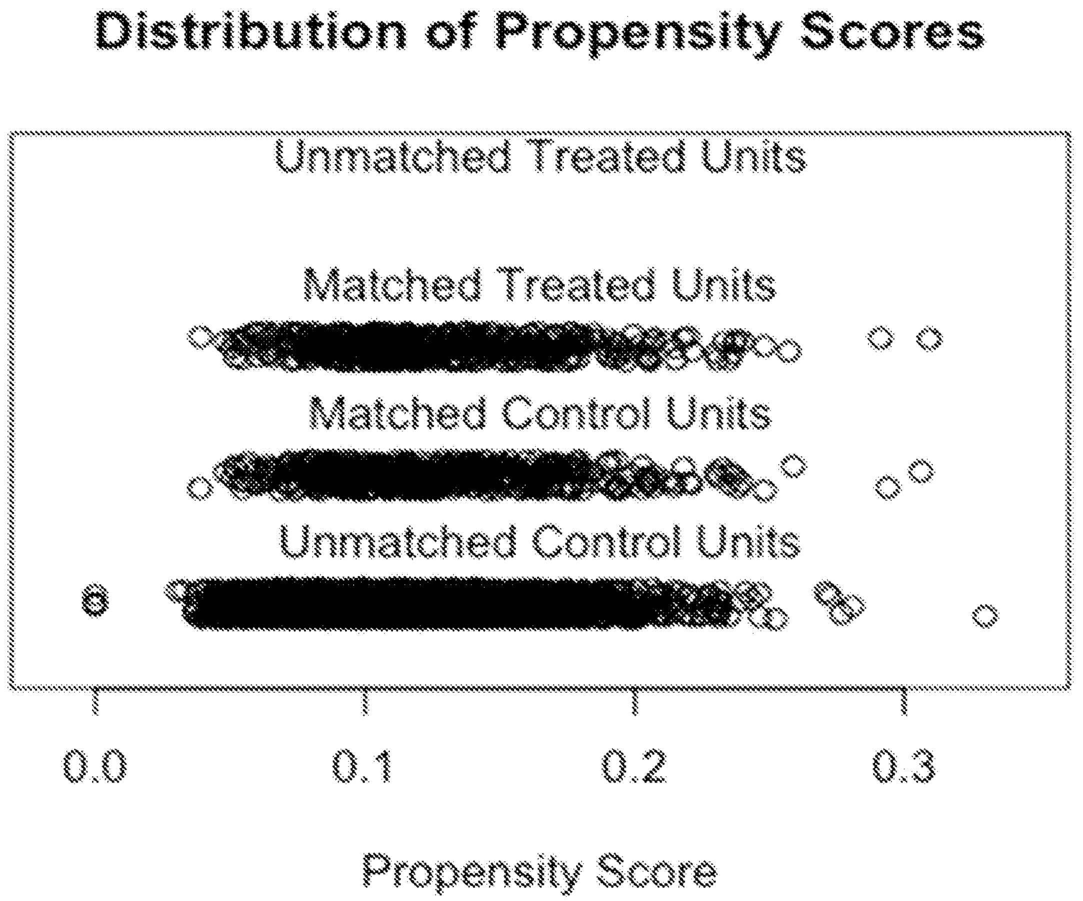
FIG. 3 illustrates distribution of propensity scores in the matched H2 antihistamine groups.

After nearest-neighbor propensity score matching, the total sample was reduced to N=936 patients, with N=468 matched patients in each study group. The H2 antihistamine study groups showed relatively similar distributions (FIG. 3). Table 12 shows that after matching, the study groups were balanced and had no significant differences in any of the demographic and comorbidities.

TABLE 12

Descriptive Statistics of PS-Matched Sample (N = 936) by Antihistamine Use Cohorts (H1 only)

| Variable | Label | H2 Antihistamine Use (N = 468) | No H2 Antihistamine Use (N = 468) | p-value |
|---|---|---|---|---|
| Age (Years) | | 64.1 (17.34) | 64.05 (17.34) | 0.964 |
| Gender | | | | 0.552 |
| | Female | 273 (58.33%) | 263 (56.2%) | |
| | Male | 195 (41.67%) | 205 (43.8%) | |
| Race | | | | 0.673 |
| | African American | 80 (17.09%) | 68 (14.53%) | |
| | Am Indian/Alaskan Native | 2 (0.43%) | 0 (0%) | |
| | Asian | 4 (0.85%) | 4 (0.85%) | |
| | Multiracial | 1 (0.21%) | 1 (0.21%) | |
| | Unknown | 19 (4.06%) | 16 (3.42%) | |
| | White | 362 (77.35%) | 379 (80.98%) | |
| Ethnicity: Hispanic/Latino | | 7 (1.5%) | 3 (0.64%) | 0.34 |
| PRISM Score | | 2.62 (1.16) | 2.58 (1.19) | 0.655 |
| Hypertension | | 353 (75.43%) | 362 (77.35%) | 0.538 |
| Diabetes | | 196 (41.88%) | 198 (42.31%) | 0.947 |
| Asthma | | 59 (12.61%) | 44 (9.4%) | 0.144 |
| COPD | | 147 (31.41%) | 139 (29.7%) | 0.619 |
| Obesity | | 83 (17.74%) | 76 (16.24%) | 0.601 |
| CAD | | 170 (36.32%) | 166 (35.47%) | 0.838 |
| Allergies | | 8 (1.71%) | 6 (1.28%) | 0.788 |

Results for the primary outcome of SARS-CoV-2 infection rates between the matched treatment groups of H2 antihistamine use and no H2 antihistamine use are shown in Table 13. After matching patients on demographics and comorbidities, there is not a significant difference in infection rates between the two groups (19.44% vs 18.38%, p-value=0.738). These results are confirmed in the multivariable logistic regression model results shown in Table 14 (OR=1.011, p-value=0.653).

TABLE 13

Positive COVID Test Result by Antihistamine Use (H2 only) - PS-Matched Sample (N = 936)

| Variable | H2 Antihistamine Use (N = 468) | No H2 Antihistamine Use (N = 468) | p-value |
|---|---|---|---|
| SARS-CoV-2 Positive Test Result | 91 (19.44%) | 86 (18.38%) | 0.738 |

TABLE 14

Multiple Logistic Regression Model for SARS-CoV-2 Infection - Antihistamine Use (H2 only)

| Covariate | Odds Ratio | 95% CI | p-value |
|---|---|---|---|
| Antihistamine Use (H2 only) | 1.011 | (0.963, 1.062) | 0.653 |
| Age | 1.001 | (0.999, 1.003) | 0.234 |
| Gender (Male) | 0.971 | (0.922, 1.023) | 0.271 |
| Race (African American) | 1.130 | (1.054, 1.21) | 0.001 |
| Race (Asian) | 0.987 | (0.755, 1.289) | 0.922 |
| Race (Am Indian/Alaskan Native) | 0.886 | (0.52, 1.509) | 0.656 |
| Race (Multiracial)) | 0.949 | (0.557, 1.616) | 0.847 |

TABLE 14-continued

Multiple Logistic Regression Model for SARS-CoV-2 Infection - Antihistamine Use (H2 only)

| Covariate | Odds Ratio | 95% CI | p-value |
|---|---|---|---|
| Race (Unknown) | 1.077 | (0.946, 1.227) | 0.263 |
| Ethnicity (Hispanic/Latino) | 1.118 | (0.88, 1.422) | 0.362 |
| Hypertension | 0.965 | (0.898, 1.037) | 0.331 |
| Diabetes | 1.033 | (0.98, 1.09) | 0.227 |
| Asthma | 0.952 | (0.878, 1.033) | 0.24 |
| COPD | 0.893 | (0.845, 0.945) | <0.001 |
| Obesity | 1.052 | (0.983, 1.127) | 0.144 |
| CAD | 0.912 | (0.862, 0.966) | 0.002 |
| Allergies | 0.866 | (0.707, 1.062) | 0.167 |
| PRISM Score | 0.950 | (0.926, 0.976) | <0.001 |

Note:
White was the reference group for race.

Of the patients who tested positive in the PS-matched sample of H2 antihistamine users, there was not a significant difference in ICU admission rates (p-value=0.591, Table 15) or ICU length of stay (p-value=0.576).

TABLE 15

ICU Admission and LOS of SARS-CoV-2 Positive Patients by Drug Use (H2 users only) - PS

| Drug Type | Variable | Drug Use | No Drug Use | P Value |
|---|---|---|---|---|
| H2 Only | | N = 91 | N = 91 | |
| | ICU Admission | 22 (24.18%) | 18 (19.78%) | 0.591 |
| | ICU LOS | 11.27 (14.96) | 14.28 (18.71) | 0.576 |

Individual Drugs Analysis

Table 16 shows the results of infection rates by individual drug use after propensity score matching on each specific drug subset. Only Hydroxyzine Use had statistically significantly different infection rates after matching ($p<0.05$). Therefore only the full results for that drug are subsequently presented.

The statistical significance associated with hydroxyzine is believed to be attributed, without being construed as limiting, to the fact that hydroxyzine is a prescription medication and is believed to be taken by patients regularly. In other words, it is believed that there is a greater patient compliance with prescription medication as compared to over the counter (OTC) medications. Unlike hydroxyzine, drugs such as cetirizine, which are available OTC, are believed to be taken less regularly and may not always be listed in a patient's record upon hospitalization (like a prescription drug would be). Accordingly, it is believed that the infection rate differences seen with hydroxyzine are statistically significant because the information about its use is more reliable as compared to other drugs listed below. Hence, even though other drugs were not necessarily recognized here as having statistically significant differences in COVID-19 infection rates, that information should not be construed as limiting, as the results for a given drug could be different (i.e., illustrate statistically significant differences in COVID-19 infection rates) under more controlled conditions (such as, consistent/regular/compliant use of the drug).

TABLE 16

Positive COVID Test Result by Individual Drug Use - PS-Matched Samples

| Drug Name | Drug Use | No Drug Use | P Value |
|---|---|---|---|
| Cetirizine | N = 256<br>46 (17.97%) | N = 256<br>51 (19.92%) | 0.652 |

TABLE 16-continued

Positive COVID Test Result by Individual Drug Use - PS-Matched Samples

| Drug Name | Drug Use | No Drug Use | P Value |
|---|---|---|---|
| Hydroxyzine | N = 206<br>26 (12.62%) | N = 206<br>42 (20.39%) | 0.047 |
| Azelastine | N = 39<br>3 (7.69%) | N = 39<br>9 (23.08%) | 0.117 |
| Fexofenadine | N = 74<br>14 (18.92%) | N = 74<br>11 (14.86%) | 0.661 |
| Loratadine | N = 311<br>58 (18.65%) | N = 311<br>56 (18.01%) | 0.917 |
| Levocetirizine | N = 13<br>2 (15.38%) | N = 13<br>0 (0%) | 0.48 |
| Diphenhydramine | N = 250<br>32 (12.8%) | N = 250<br>47 (18.8%) | 0.086 |
| Chlorpheniramine | N = 6<br>1 (16.67%) | N = 6<br>2 (33.33%) | >0.999 |
| Brompheniramine | N = 3<br>1 (33.33%) | N = 3<br>1 (33.33%) | >0.999 |
| Olopatadine | N = 32<br>6 (18.75%) | N = 32<br>6 (18.75%) | >0.999 |
| Ketotifen | N = 10<br>0 (0%) | N = 10<br>3 (30%) | 0.211 |
| Famotidine | N = 461<br>87 (18.87%) | N = 461<br>92 (19.96%) | 0.739 |
| Cimetidine | N = 14<br>5 (35.71%) | N = 14<br>4 (28.57%) | >0.999 |
| Ranitidine | N = 170<br>26 (15.29%) | N = 170<br>30 (17.65%) | 0.661 |

Note:
The following drugs were not considered due to low counts: clemastine, desloratadine, rupatadine, carbinoxamine, triprolidine, astemizole, levocabastine, bepotastine, ebastine, and nizatidine.

Hydroxyzine Use

Demographics and comorbidities of the total sample by hydroxyzine use are presented in Table 17. Several variables including age, gender, PRISM score, obesity, and CAD are unbalanced between the hydroxyzine groups, with those using hydroxyzine having higher rates of comorbidities.

TABLE 17

Descriptive Statistics of Total Sample by Hydroxyzine Use

| Variable | Label | Hydroxyzine Use (N = 206) | No Hydroxyzine Use (N =3974) | P Value |
|---|---|---|---|---|
| Age (Years) | | 56.37 (18.88) | 64.89 (17.89) | <0.001 |
| Gender | | | | <0.001 |
| | Female | 134 (65.05%) | 2048 (51.53%) | |
| | Male | 72 (34.95%) | 1926 (48.47%) | |
| Race | | | | 0.325 |
| | African American | 40 (19.42%) | 725 (18.24%) | |
| | Am Indian/Alaskan Native | 2 (0.97%) | 9 (0.23%) | |
| | Asian | 1 (0.49%) | 55 (1.38%) | |
| | Hawaiian/Pac Islander | 0 (0%) | 3 (0.08%) | |
| | Multiracial | 1 (0.49%) | 12 (0.3%) | |
| | Unknown | 5 (2.43%) | 133 (3.35%) | |
| | White | 157 (76.21%) | 3037 (76.42%) | |
| Ethnicity: Hispanic/Latino | | 3 (1.46%) | 80 (2.01%) | 0.798 |
| PRISM Score | | 3.11 (1.06) | 2.76 (1.17) | <0.001 |
| Hypertension | | 137 (66.5%) | 2763 (69.53%) | 0.401 |
| Diabetes | | 81 (39.32%) | 1514 (38.1%) | 0.78 |
| Asthma | | 25 (12.14%) | 398 (10.02%) | 0.387 |
| COPD | | 53 (25.73%) | 1023.74%) | >0.999 |
| Obesity | | 51 (24.76%) | 721 (18.14%) | 0.022 |
| CAD | | 54 (26.21%) | 1329 (33.44%) | 0.038 |
| Allergies | | 1 (0.49%) | 49 (1.23%) | 0.516 |

Figure 4:
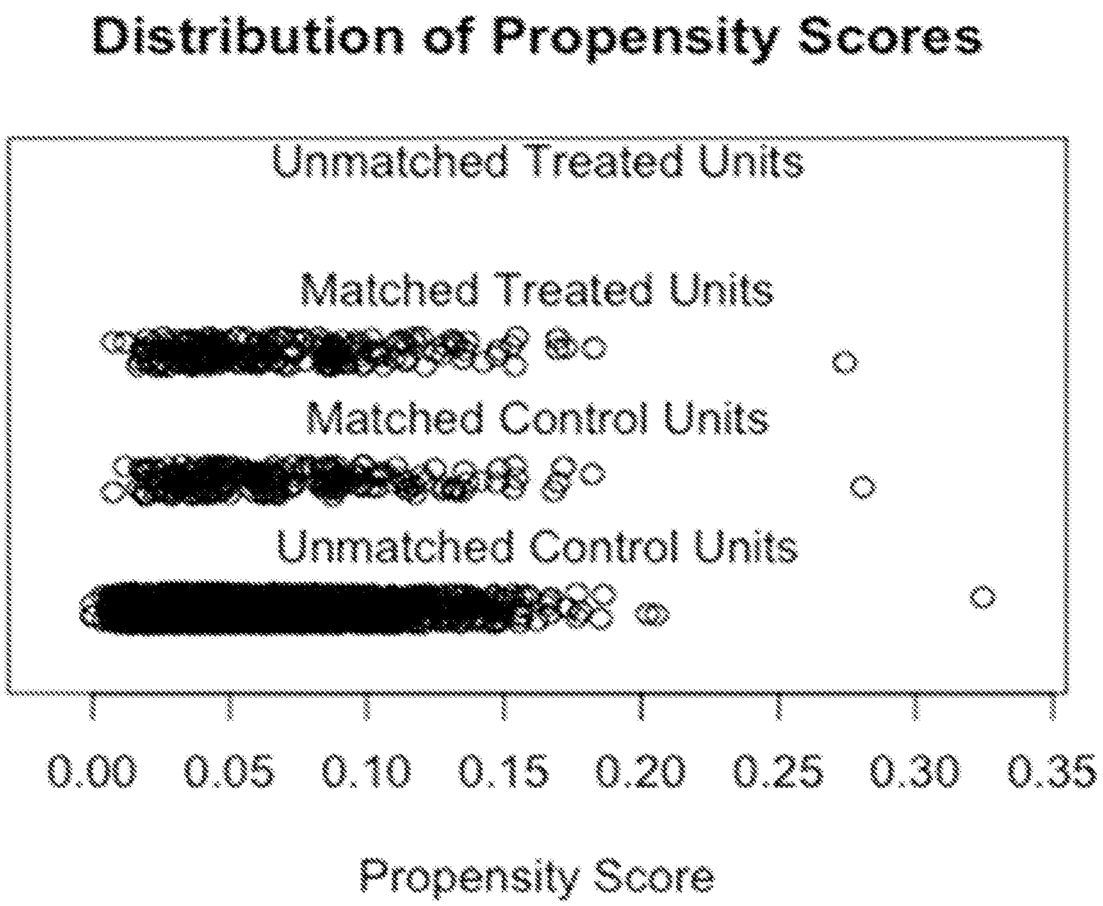
FIG. 4 illustrates distribution of propensity scores in the matched hydroxyzine groups.

After nearest-neighbor propensity score matching, the total sample was reduced to N=412 patients, with N=206 matched patients in each study group. The hydroxyzine study groups showed relatively similar distributions (FIG. 4). Table 18 shows that after matching, the study groups were balanced and had no significant differences in any of the demographic and comorbidities.

TABLE 18

Descriptive Statistics of PS-Matched Sample by Hydroxyzine Use Cohorts

| Variable | Label | Hydroxyzine Use (N = 206) | No Hydroxyzine Use (N = 206) | P Value |
|---|---|---|---|---|
| Age (Years) | | 56.37 (18.88) | 57.35 (19.12) | 0.601 |
| Gender | | | | 0.463 |
| | Female | 134 (65.05%) | 142 (68.93%) | |
| | Male | 72 (34.95%) | 64 (31.07%) | |
| Race | | | | >0.999 |
| | African American | 40 (19.42%) | 40 (19.42%) | |
| | Am Indian/Alaskan Native | 2 (0.97%) | 2 (0.97%) | |
| | Asian | 1 (0.49%) | 2 (0.97%) | |
| | Multiracial | 1 (0.49%) | 0 (0%) | |
| | Unknown | 5 (2.43%) | 4 (1.94%) | |
| | White | 157 (76.21%) | 158 (76.7%) | |
| Ethnicity: Hispanic/Latino | | 3 (1.46%) | 1 (0.49%) | 0.623 |
| PRISM Score | | 3.11 (1.06) | 3.11 (1.16) | 0.965 |
| Hypertension | | 137 (66.5%) | 138 (66.99%) | >0.999 |
| Diabetes | | 81 (39.32%) | 80 (38.83%) | >0.999 |
| Asthma | | 25 (12.14%) | 22 (10.68%) | 0.757 |
| COPD | | 53 (25.73%) | 59 (28.64%) | 0.58 |
| Obesity | | 51 (24.76%) | 52 (25.24%) | >0.999 |
| CAD | | 54 (26.21%) | 57 (27.67%) | 0.824 |
| Allergies | | 1 (0.49%) | 1 (0.49%) | >0.999 |

Results for the primary outcome of SARS-CoV-2 infection rates between the matched treatment groups of hydroxyzine use and no hydroxyzine use are shown in Table 19. After matching patients on demographics and comorbidities, there is a significant difference in infection rates between the two groups (12.62% vs 20.39%, p-value=0.047). These results are confirmed in the multivariable logistic regression model results shown in Table 20 (OR=0.919, p-value=0.02).

TABLE 19

Positive COVID Test Result by Hydroxyzine Use - PS-Matched Sample

| Variable | Hydroxyzine Use (N = 206) | No Hydroxyzine Use (N = 206) | P Value |
|---|---|---|---|
| SARS-CoV-2 Positive Test Result | 26 (12.62%) | 42 (20.39%) | 0.047 |

TABLE 20

Multiple Logistic Regression Model for SARS-CoV-2 Infection - Hydroxyzine Use Only

| Covariate | Odds Ratio | 95% CI | p-value |
|---|---|---|---|
| Hydroxyzine Use | 0.919 | (0.856, 0.987) | 0.020 |
| Age | 0.999 | (0.997, 1.002) | 0.628 |
| Gender (Male) | 1.034 | (0.956, 1.119) | 0.407 |
| Race (African American) | 1.160 | (1.056, 1.273) | 0.002 |
| Race (Asian) | 0.812 | (0.533, 1.239) | 0.335 |
| Race (Am Indian/Alaskan Native) | 1.103 | (0.766, 1.588) | 0.599 |
| Race (Multiracial)) | 1.116 | (0.367, 3.395) | 0.847 |
| Race (Unknown) | 0.978 | (0.764, 1.252) | 0.858 |

TABLE 20-continued

Multiple Logistic Regression Model for SARS-CoV-2 Infection - Hydroxyzine Use Only

| Covariate | Odds Ratio | 95% CI | p-value |
|---|---|---|---|
| Ethnicity (Hispanic/Latino) | 1.169 | (0.768, 1.78) | 0.467 |
| Hypertension | 1.014 | (0.923, 1.114) | 0.779 |
| Diabetes | 1.023 | (0.943, 1.11) | 0.588 |
| Asthma | 0.985 | (0.879, 1.105) | 0.801 |
| COPD | 0.931 | (0.854, 1.015) | 0.106 |
| Obesity | 1.008 | (0.923, 1.1) | 0.861 |
| CAD | 0.971 | (0.885, 1.066) | 0.541 |
| Allergies | 0.751 | (0.361, 1.563) | 0.445 |
| PRISM Score | 0.955 | (0.915, 0.996) | 0.032 |

Of the patients who tested positive in the PS-matched sample of hydroxyzine users, there was not a significant difference in ICU admission rates (p-value>0.999, Table 21) or ICU length of stay (p-value=0.322).

TABLE 21

ICU Admission and LOS of SARS-CoV-2 Positive Patients by Drug Use - PS

| Drug Type | Variable | Drug Use | No Drug Use | P Value |
|---|---|---|---|---|
| Hydroxyzine | | N = 26 | N = 42 | |
| | ICU Admission | 5 (19.23%) | 8 (19.05%) | >0.999 |
| | ICU LOS | 22.4 (26.43) | 10.38 (15.81) | 0.322 |

Example 2

Antihistamines as ACE2 Receptor Modulators

The results of example 1 illustrated that at least use of hydroxyzine contributed to statistically significant differences (with statistical significance being based on the p value being less than 0.05) in COVID-19 infection rates (lower infection rates in individuals who used hydroxyzine).

In this example, the activity of several antihistamines (Diphenhydramine, R-Azelastine, S-Azelastine, and Hydroxyzine, S-Cetirizine, and R-Cetirizine) on ACE2 receptor was assessed via an ACE2 activity assay. It is believed without being construed as limiting that the antihistamines interacts with and/or modulates the ACE2 receptor (e.g., by inhibiting and/or activating the ACE2 receptor) such that the spike protein (and correspondingly coronavirus or COVID-19) would not be able to enter the cells.

The ACE2 activity assay was based on the use of the fluorogenic peptide substrate VI [7Mca-Y-V-A-D-A-PK (Knp)-OH] (also referred to as "SEQ ID NO: 1" or "Mca-Tyr-Val-Ala-Asp-Ala-Pro-Lys(Dnp)-OH trifluoroacetate salt").

ACE2 removes the c-terminal dinitrophenyl moiety that quenches the inherent fluorescence of the 7-methoxycoumain group, resulting in an increase in fluorescence. Human recombinant ACE2 was obtained along with its fluorogenic substrate from R&D systems, Minneapolis, USA.

The enzymatic activity was measured in a total volume of 100 μL using a fluorescence plate reader at an excitation wavelength of 320 nm and emission wavelength of 405 nm. All assays were performed in duplicate in ACE2 buffer containing 1M NaCl, 75 mM Tris-HCl, and 0.5 μM ZnCl2, at pH 7.4, 0.5 ng ACE2 enzyme, 20 uM substrate, drugs of various concentrations and the SARS Cov2 spike protein (1.8 ug). Samples were read at 37° C. for every 36 seconds for 60 minutes immediately after the addition of fluorogenic peptide substrate using a Spectra Max Gemini EM Florescence Reader (Molecular Devices).

The Spike Protein used contained both, the S1 and S2 domains, and could bind to ACE2. Details of the Spike Protein were available from https://www.genscript.com/protein/Z03479-SARS_CoV_2_Spike_protein_RBD_His_Tag_.html. According to GenScript Datasheet version 2020331, it was described SARS-Cov-2 Spike Protein (RBD, His Tag), with the following description:

SARS-CoV-2 (Severe Acute Respiratory Syndrome Coronavirus 2) also known as 2019-nCoV (2019 Novel Coronavirus) is a virus that causes illnesses ranging from the common cold to severe diseases. SARS-CoV-2 Spike Protein is composed of S1 domain and S2 domain. S1 contains a receptor-binding domain (RBD) that can specifically bind to angiotensin-converting enzyme 2 (ACE2), the receptor on target cells. It is believed that SARS-CoV-2 Spike Protein (RBD) has potential value for the diagnosis of the virus.

The following additional details were included in the datasheet:

Cat. No. Z03479-100; Z03479-500; Z03479-1
Size: 100 μg/500 μg/1 mg
Synonyms: SARS-CoV-2 SP RBD; 2019-nCoV RBD
Source: Sf9 insect cells
Species: SARS-CoV-2
Biological Activity: SARS-CoV-2 Spike Protein (RBD, His Tag) can bind with Human ACE2 in functional ELISA assay.
Molecular Weight: predicted molecular weight: 25 KD
Tag: His Tag
Formulation: Liquid
Purity: >90% as analyzed by SDS-PAGE
Storage Buffer: PBS, pH 7.2
Storage: The product can be stored at −20° C. or below. Avoid repeated freezing and thawing cycles. The shelf life of the product is unspecified.
Sequence: Accession#QHD43416.1(Pro330-Ser530)

Diphenhydramine

Figure 5A:
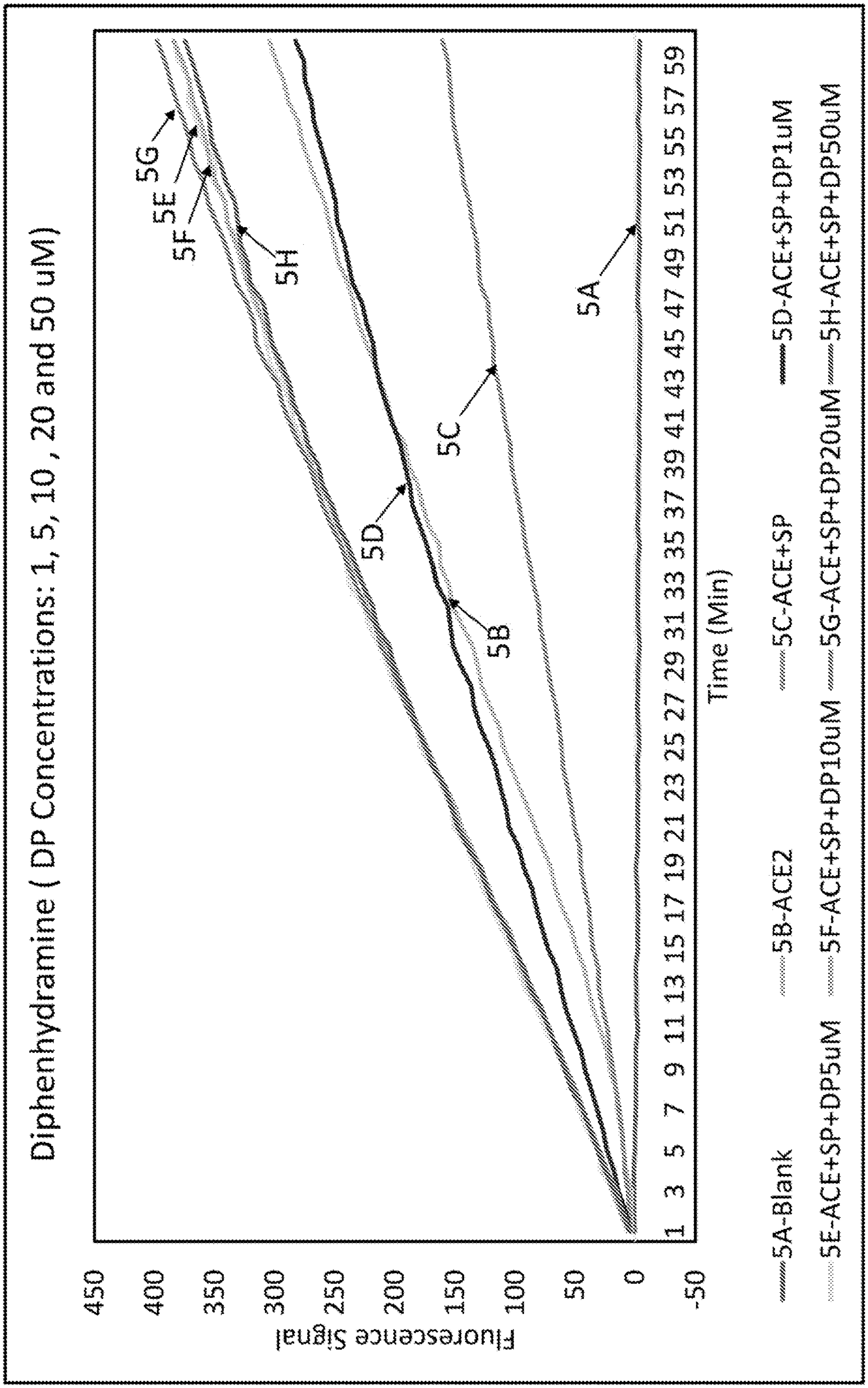
FIG. 5A illustrates ACE2 modulation activity of diphenhydramine at diphenhydramine concentrations ranging from 1 μM to 50 μM.

In FIG. 5A, the fluorescent signal of eight samples were assessed over a duration of 60 minutes. The composition of the samples is summarized in Table 22A below.

TABLE 22A

| No. | Sample |
|---|---|
| 5A | Blank |
| 5B | ACE2 Receptor |
| 5C | ACE2 receptor mixed with 3 μL of the Spike Protein |
| 5D | ACE2 receptor mixed with 3 μL of the Spike Protein and Diphenhydramine at an amount effective to arrive at a concentration of 1 μM |
| 5E | ACE2 receptor mixed with 3 μL of the Spike Protein and Diphenhydramine at an amount effective to arrive at a concentration of 5 μM |
| 5F | ACE2 receptor mixed with 3 μL of the Spike Protein and Diphenhydramine at an amount effective to arrive at a concentration of 10 μM |
| 5G | ACE2 receptor mixed with 3 μL of the Spike Protein and Diphenhydramine at an amount effective to arrive at a concentration of 20 μM |
| 5H | ACE2 receptor mixed with 3 μL of the Spike Protein and Diphenhydramine at an amount effective to arrive at a concentration of 50 μM |

Figure 5B:
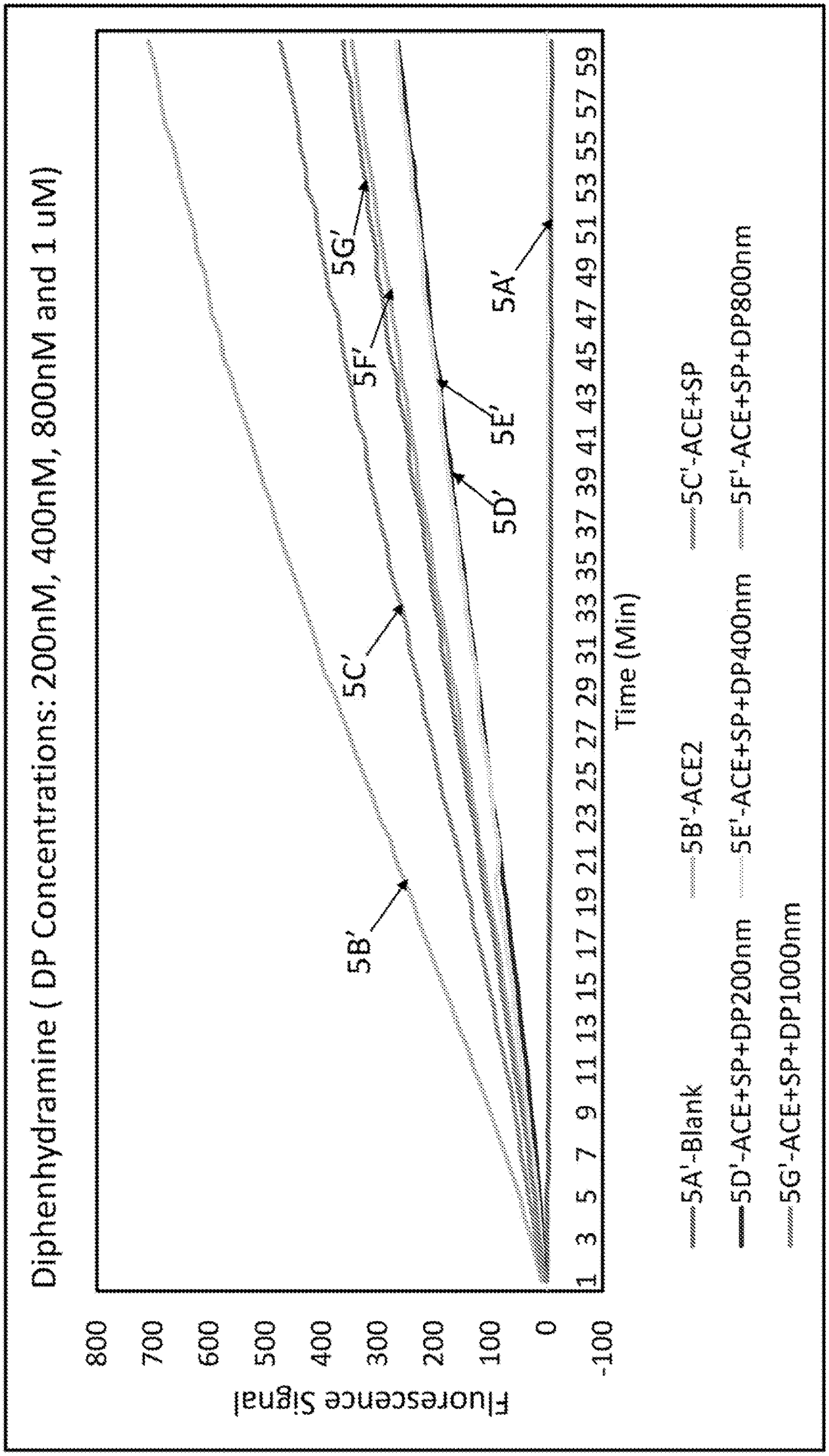
FIG. 5B illustrates ACE2 modulation activity of diphenhydramine at diphenhydramine concentrations ranging from 200 nM to 1 μM.

In FIG. 5B, the fluorescent signal of seven samples were assessed over a duration of 60 minutes. The composition of the samples is summarized in Table 22B below.

TABLE 22B

| No. | Sample |
|---|---|
| 5A' | Blank |
| 5B' | ACE2 Receptor |
| 5C' | ACE2 receptor mixed with 3 μL of the Spike Protein |
| 5D' | ACE2 receptor mixed with 3 μL of the Spike Protein and Diphenhydramine at an amount effective to arrive at a concentration of 200 nM |
| 5E' | ACE2 receptor mixed with 3 μL of the Spike Protein and Diphenhydramine at an amount effective to arrive at a concentration of 400 nM |
| 5F' | ACE2 receptor mixed with 3 μL of the Spike Protein and Diphenhydramine at an amount effective to arrive at a concentration of 800 nM |
| 5G' | ACE2 receptor mixed with 3 μL of the Spike Protein and Diphenhydramine at an amount effective to arrive at a concentration of 1 μM (1000 nM) |

As can be seen in FIGS. 5A and 5B, the ACE2 receptor emitted a fluorescence signal (Samples 5B and 5B'). Upon addition of the Spike Protein (Samples 5C and 5C'), the fluorescence signal decreased, indicating that the Spike Protein inhibited the ACE2 receptor. Upon further addition of Diphenhydramine in an amount effective to reach a 1 μM-50 μM concentration of Diphenhydramine (Samples 5D, 5E, 5F, 5G, and 5H in FIG. 5A), the fluorescence signal increased. Upon further addition of Diphenhydramine in an amount effective to reach a 200 nM-1 μM concentration of Diphenhydramine (Samples 5D', 5E', 5F', and 5G' in FIG. 5B), the fluorescence signal decreased further. A Diphenhydramine concentration of 1 μM appeared to be a transition point from inhibiting the ACE2 receptor (at Diphenhydramine concentrations lower than 1 μM) to activating the ACE2 receptor (at Diphenhydramine concentrations higher than 1 μM).

It is believed, without being construed as limiting, that the fluorescence signal results from FIGS. 5A and 5B suggest that addition of Diphenhydramine, in certain embodiments, reverses the effect of the Spike Protein on the ACE2 receptor and/or that addition of Diphenhydramine, in certain embodiments, interferes with/prevent the ability of the Spike Protein to bind/inhibit the ACE2 receptor. It is believed, without being construed as limiting, that FIGS. 5A and 5B illustrated that Diphenhydramine modulates the ACE2 receptor, such that Diphenhydramine may be, in certain embodiments, an ACE2 receptor inhibitor, an ACE2 receptor activator, or a combination thereof.

R-Azelastine

Figure 6A:
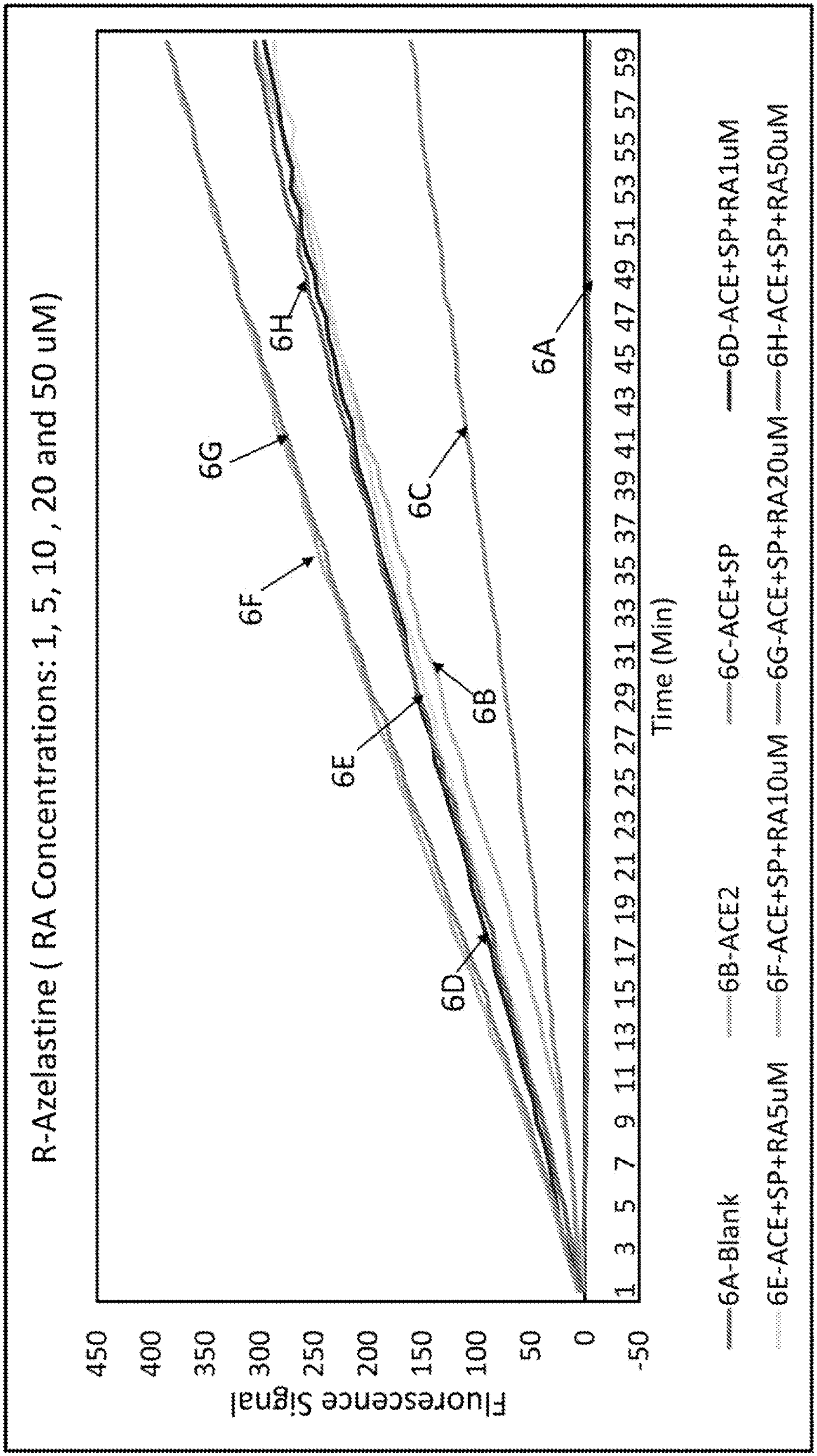
FIG. 6A illustrates ACE2 modulation activity of R-Azelastine at R-Azelastine concentrations ranging from 1 μM to 50 μM.

In FIG. 6A, the fluorescent signal of eight samples were assessed over a duration of 60 minutes. The composition of the samples is summarized in Table 23A below.

TABLE 23A

| No. | Sample |
|---|---|
| 6A | Blank |
| 6B | ACE2 Receptor |
| 6C | ACE2 receptor mixed with 3 μL of the Spike Protein |
| 6D | ACE2 receptor mixed with 3 μL of the Spike Protein and R-Azelastine at an amount effective to arrive at a concentration of 1 μM |
| 6E | ACE2 receptor mixed with 3 μL of the Spike Protein and R-Azelastine at an amount effective to arrive at a concentration of 5 μM |
| 6F | ACE2 receptor mixed with 3 μL of the Spike Protein and R-Azelastine at an amount effective to arrive at a concentration of 10 μM |
| 6G | ACE2 receptor mixed with 3 μL of the Spike Protein and R-Azelastine at an amount effective to arrive at a concentration of 20 μM |
| 6H | ACE2 receptor mixed with 3 μL of the Spike Protein and R-Azelastine at an amount effective to arrive at a concentration of 50 μM |

Figure 6B:
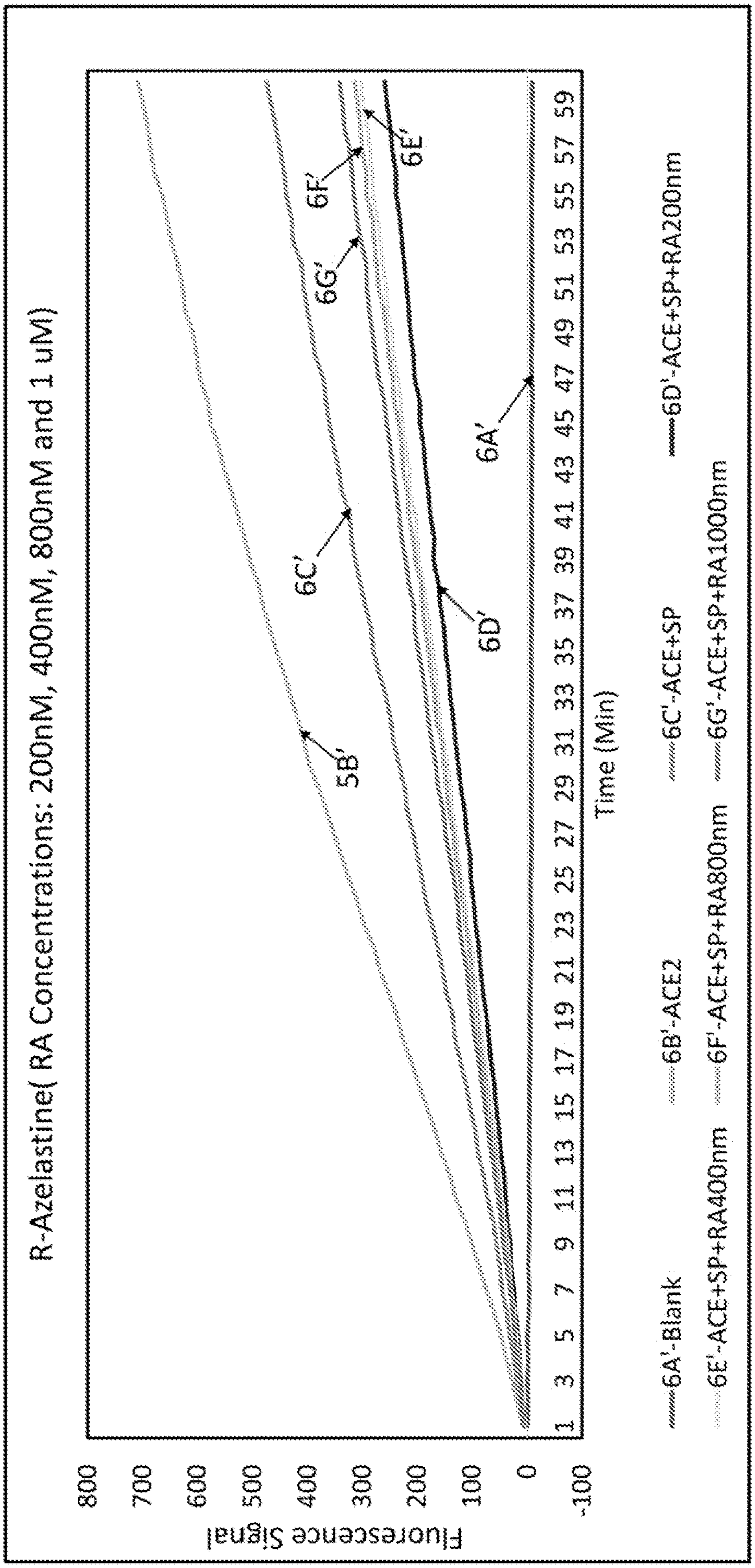
FIG. 6B illustrates ACE2 modulation activity of R-Azelastine at R-Azelastine concentrations ranging from 200 nM to 1 μM.

In FIG. 6B, the fluorescent signal of seven samples were assessed over a duration of 60 minutes. The composition of the samples is summarized in Table 23B below.

TABLE 23B

| No. | Sample |
|---|---|
| 6A' | Blank |
| 6B' | ACE2 Receptor |
| 6C' | ACE2 receptor mixed with 3 μL of the Spike Protein |
| 6D' | ACE2 receptor mixed with 3 μL of the Spike Protein and R-Azelastine at an amount effective to arrive at a concentration of 200 nM |
| 6E' | ACE2 receptor mixed with 3 μL of the Spike Protein and R-Azelastine at an amount effective to arrive at a concentration of 400 nM |
| 6F' | ACE2 receptor mixed with 3 μL of the Spike Protein and R-Azelastine at an amount effective to arrive at a concentration of 800 nM |
| 6G' | ACE2 receptor mixed with 3 μL of the Spike Protein and R-Azelastine at an amount effective to arrive at a concentration of 1 μM (1000 nM) |

As can be seen in FIGS. 6A and 6B, the ACE2 receptor emitted a fluorescence signal (Samples 6B and 6B'). Upon addition of the Spike Protein (Samples 6C and 6C'), the fluorescence signal decreased, indicating that the Spike Protein inhibited the ACE2 receptor. Upon further addition of R-Azelastine in an effective amount to reach and R-Azelastine concentration of 1 μM-50 μM (Samples 6D, 6E, 6F, 6G, and 6H in FIG. 6A), the fluorescence signal increased. Upon further addition of R-Azelastine in an amount effective to reach a 200 nM-1 μM concentration of R-Azelastine (Samples 6D', 6E', 6F', and 6G' in FIG. 6B), the fluorescence signal decreased further. A R-Azelastine concentration of 1 μM appeared to be a transition point from inhibiting the ACE2 receptor (at R-Azelastine concentrations lower than 1 μM) to activating the ACE2 receptor (at R-Azelastine concentrations higher than 1 μM).

It is believed, without being construed as limiting, that the fluorescence signal results from FIGS. 6A and 6B suggest that addition of R-Azelastine, in certain embodiments, reverses the effect of the Spike Protein on the ACE2 receptor and/or that addition of R-Azelastine, in certain embodiments, interferes with/prevent the ability of the Spike Protein to bind/inhibit the ACE2 receptor. It is believed, without being construed as limiting, that FIGS. 6A and 6B illustrate that R-Azelastine modulates the ACE2 receptor, such that R-Azelastine may be, in certain embodiments, an ACE2 receptor inhibitor, an ACE2 receptor activator, or a combination thereof.

S-Azelastine

Figure 7A:
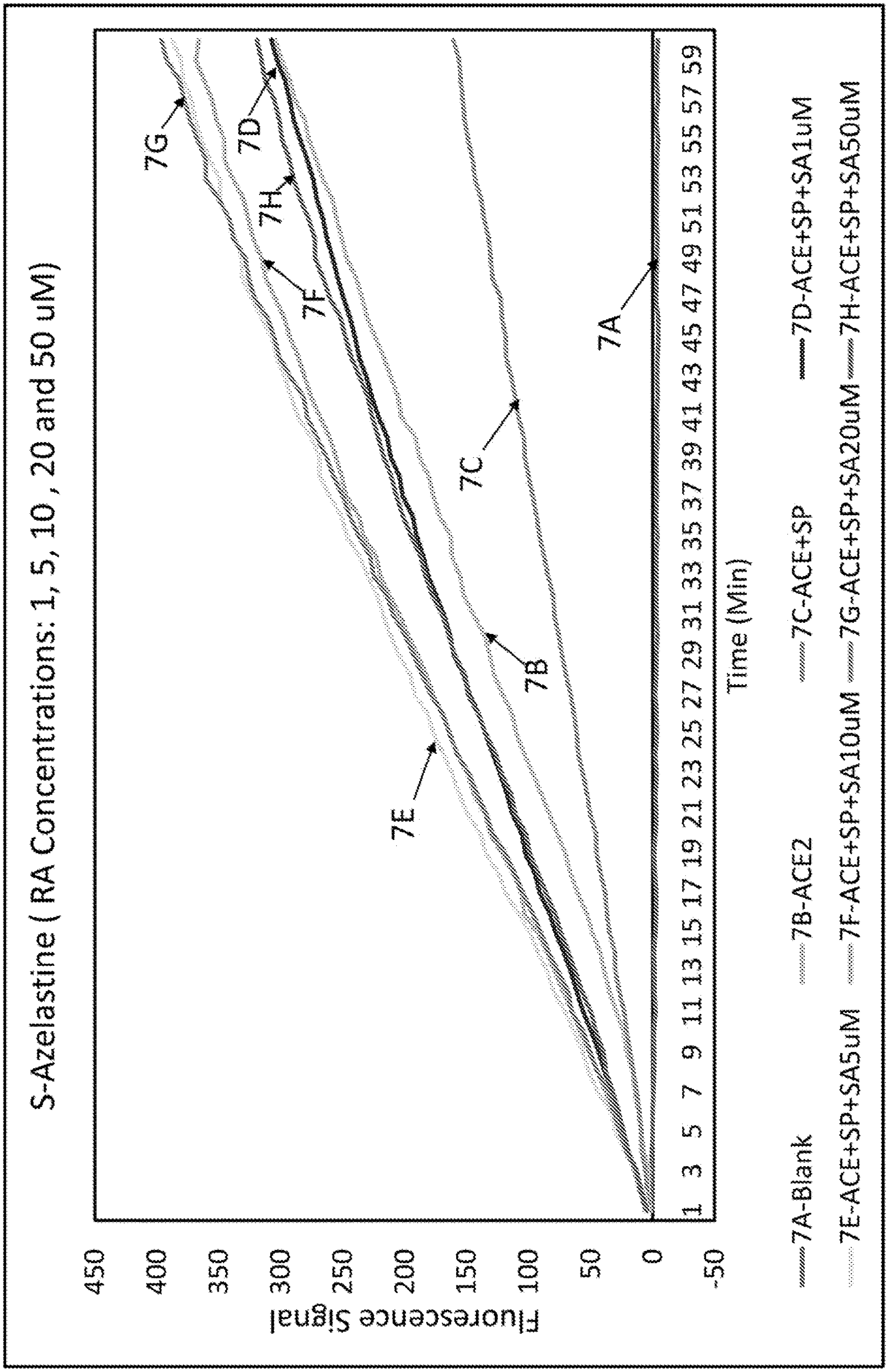
FIG. 7A illustrates ACE2 modulation activity of S-Azelastine at S-Azelastine concentrations ranging from 1 μM to 50 μM.

In FIG. 7A, the fluorescent signal of eight samples were assessed over a duration of 60 minutes. The composition of the samples is summarized in Table 24A below.

TABLE 24A

| No. | Sample |
|---|---|
| 7A | Blank |
| 7B | ACE2 Receptor |
| 7C | ACE2 receptor mixed with 3 μL of the Spike Protein |
| 7D | ACE2 receptor mixed with 3 μL of the Spike Protein and S-Azelastine at an amount effective to arrive at a concentration of 1 μM |
| 7E | ACE2 receptor mixed with 3 μL of the Spike Protein and S-Azelastine at an amount effective to arrive at a concentration of 5 μM |
| 7F | ACE2 receptor mixed with 3 μL of the Spike Protein and S-Azelastine at an amount effective to arrive at a concentration of 10 μM |
| 7G | ACE2 receptor mixed with 3 μL of the Spike Protein and S-Azelastine at an amount effective to arrive at a concentration of 20 μM |
| 7H | ACE2 receptor mixed with 3 μL of the Spike Protein and S-Azelastine at an amount effective to arrive at a concentration of 50 μM |

Figure 7B:
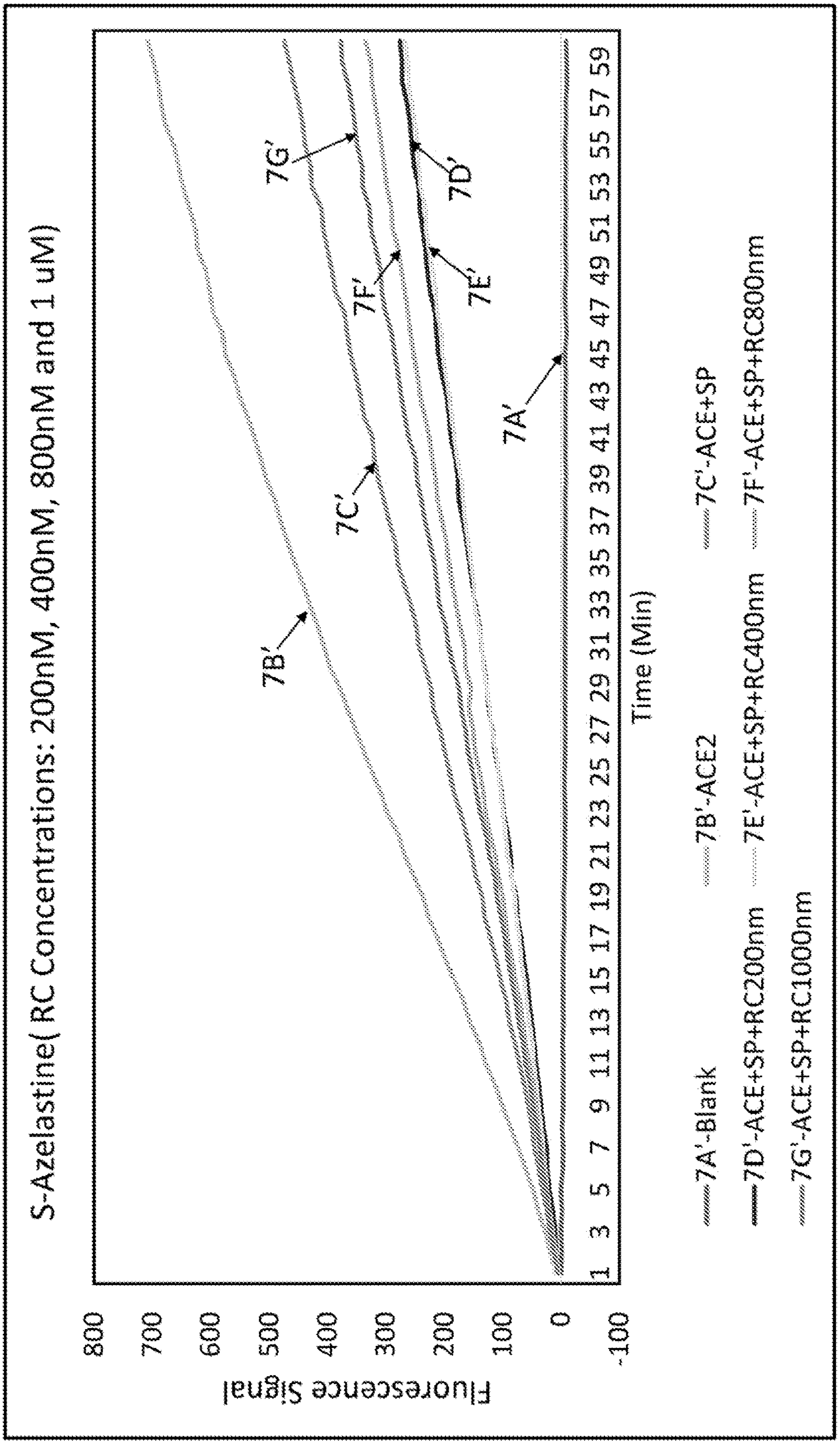
FIG. 7B illustrates ACE2 modulation activity of S-Azelastine at S-Azelastine concentrations ranging from 200 nM to 1 μM.

In FIG. 7B, the fluorescent signal of seven samples were assessed over a duration of 60 minutes. The composition of the samples is summarized in Table 24B below.

TABLE 24B

| No. | Sample |
|---|---|
| 7A' | Blank |
| 7B' | ACE2 Receptor |
| 7C' | ACE2 receptor mixed with 3 μL of the Spike Protein |
| 7D' | ACE2 receptor mixed with 3 μL of the Spike Protein and S-Azelastine at an amount effective to arrive at a concentration of 200 nM |
| 7E' | ACE2 receptor mixed with 3 μL of the Spike Protein and S-Azelastine at an amount effective to arrive at a concentration of 400 nM |
| 7F' | ACE2 receptor mixed with 3 μL of the Spike Protein and S-Azelastine at an amount effective to arrive at a concentration of 800 nM |

TABLE 24B-continued

| No. | Sample |
|---|---|
| 7G' | ACE2 receptor mixed with 3 μL of the Spike Protein and S-Azelastine at an amount effective to arrive at a concentration of 1 μM (1000 nM) |

As can be seen in FIGS. 7A and 7B, the ACE2 receptor emitted a fluorescence signal (Samples 7B and 7B'). Upon addition of the Spike Protein (Samples 7C and 7C'), the fluorescence signal decreased, indicating that the Spike Protein inhibited the ACE2 receptor. Upon further addition of S-Azelastine in an effective amount to reach and S-Azelastine concentration of 1 μM-50 μM (Samples 7D, 7E, 7F, 7G, and 7H in FIG. 7A), the fluorescence signal increased. Upon further addition of S-Azelastine in an amount effective to reach a 200 nM-1 μM concentration of S-Azelastine (Samples 7D', 7E', 7F', and 7G' in FIG. 7B), the fluorescence signal decreased further. A S-Azelastine concentration of 1 μM appeared to be a transition point from inhibiting the ACE2 receptor (at S-Azelastine concentrations lower than 1 μM) to activating the ACE2 receptor (at S-Azelastine concentrations higher than 1 μM).

It is believed, without being construed as limiting, that the fluorescence signal results from FIGS. 7A and 7B suggest that addition of S-Azelastine, in certain embodiments, reverses the effect of the Spike Protein on the ACE2 receptor and/or that addition of S-Azelastine, in certain embodiments, interferes with/prevent the ability of the Spike Protein to bind/inhibit the ACE2 receptor. It is believed, without being construed as limiting, that FIGS. 7A and 7B illustrate that S-Azelastine modulates the ACE2 receptor, such that S-Azelastine may be, in certain embodiments, an ACE2 receptor inhibitor, an ACE2 receptor activator, or a combination thereof.

Hydroxyzine

Figure 8:
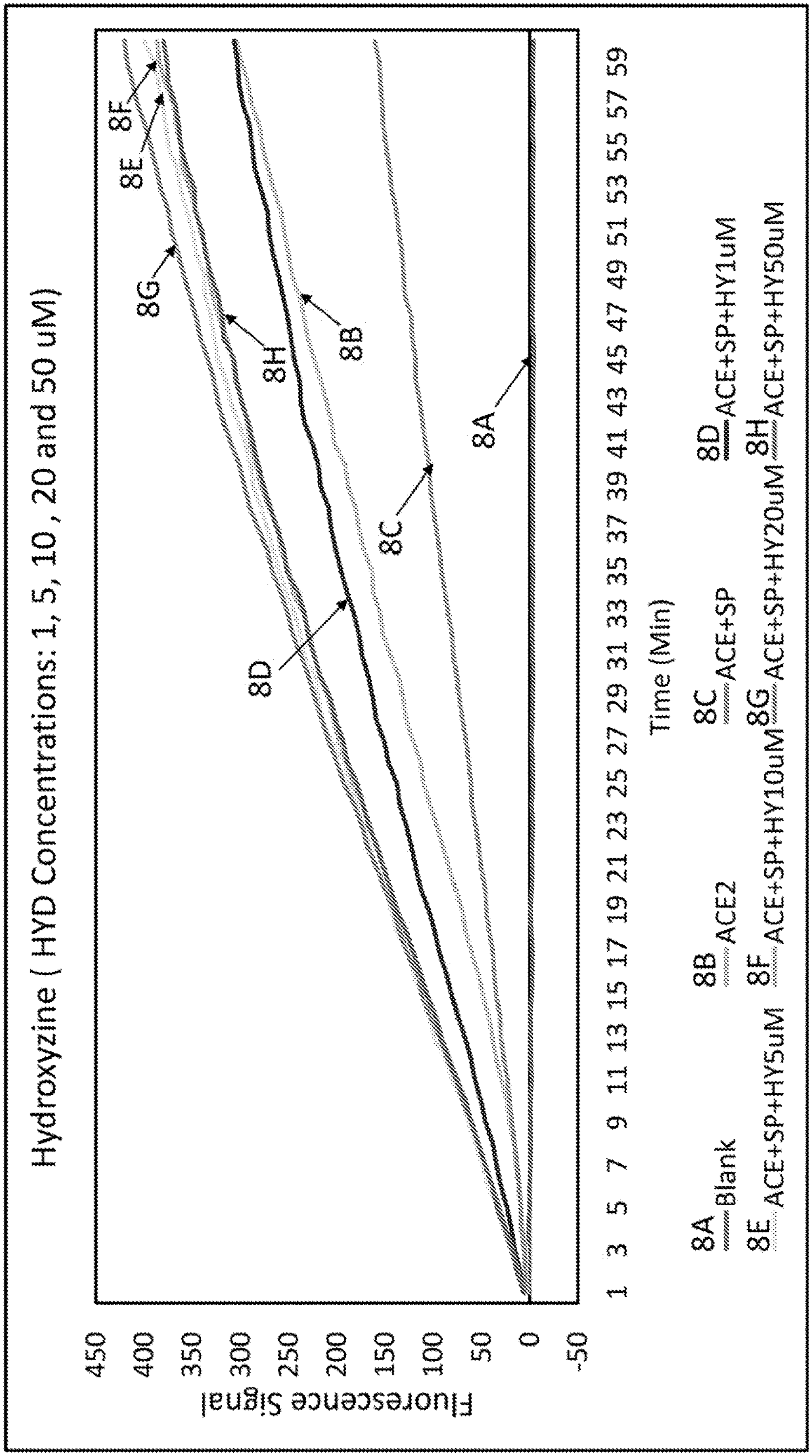
FIG. 8 illustrates ACE2 modulation activity of hydroxyzine.

In FIG. 8, the fluorescent signal of eight samples were assessed over a duration of 60 minutes. The composition of the samples is summarized in Table 25 below.

TABLE 25

| No. | Sample |
|---|---|
| 8A | Blank |
| 8B | ACE2 Receptor |
| 8C | ACE2 receptor mixed with 3 μL of the Spike Protein |
| 8D | ACE2 receptor mixed with 3 μL of the Spike Protein and Hydroxyzine at an amount effective to arrive at a concentration of 1 μM |
| 8E | ACE2 receptor mixed with 3 μL of the Spike Protein and Hydroxyzine at an amount effective to arrive at a concentration of 5 μM |
| 8F | ACE2 receptor mixed with 3 μL of the Spike Protein and Hydroxyzine at an amount effective to arrive at a concentration of 10 μM |
| 8G | ACE2 receptor mixed with 3 μL of the Spike Protein and Hydroxyzine at an amount effective to arrive at a concentration of 20 μM |
| 8H | ACE2 receptor mixed with 3 μL of the Spike Protein and Hydroxyzine at an amount effective to arrive at a concentration of 50 μM |

As can be seen in FIG. 8, the ACE2 receptor emitted a fluorescence signal (Sample 8B). Upon addition of the Spike Protein (Sample 8C), the fluorescence signal decreased, indicating that the Spike Protein inhibited the ACE2 receptor. Upon further addition of Hydroxyzine (Samples 8D, 8E, 8F, 8G, and 8H), the fluorescence signal increased. It is believed, without being construed as limiting, that the fluorescence signal results from Samples 8D through 8H suggests that addition of Hydroxyzine reverses the effect of the Spike Protein on the ACE2 receptor and/or that addition of Hydroxyzine interferes with/prevent the ability of the Spike Protein to bind/inhibit the ACE2 receptor. It is believed, without being construed as limiting, that FIG. 8 illustrates that Hydroxyzine modulates the ACE2 receptor, such that Hydroxyzine may be an ACE2 receptor inhibitor, an ACE2 receptor activator, or a combination thereof.

S-Cetirizine

Figure 9:
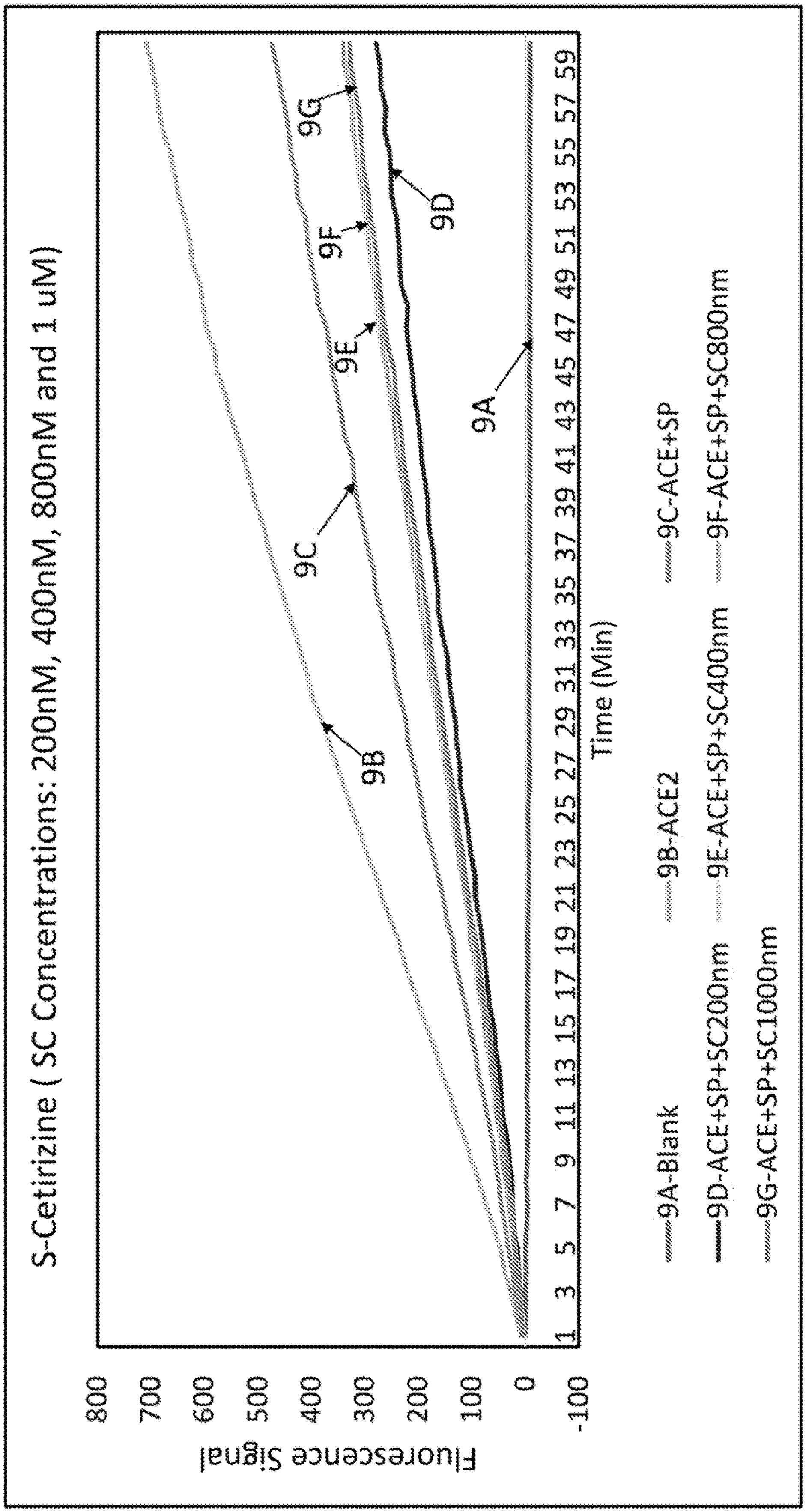
FIG. 9 illustrates ACE2 modulation activity of S-Cetrizine.

In FIG. 9, the fluorescent signal of seven samples were assessed over a duration of 60 minutes. The composition of the samples is summarized in Table 26 below.

TABLE 26

| No. | Sample |
|---|---|
| 9A | Blank |
| 9B | ACE2 Receptor |
| 9C | ACE2 receptor mixed with 3 μL of the Spike Protein |
| 9D | ACE2 receptor mixed with 3 μL of the Spike Protein and S-Cetirizine at an amount effective to arrive at a concentration of 200 nM |
| 9E | ACE2 receptor mixed with 3 μL of the Spike Protein and S-Cetirizine at an amount effective to arrive at a concentration of 400 nM |
| 9F | ACE2 receptor mixed with 3 μL of the Spike Protein and S-Cetirizine at an amount effective to arrive at a concentration of 800 nM |
| 9G | ACE2 receptor mixed with 3 μL of the Spike Protein and S-Cetirizine at an amount effective to arrive at a concentration of 1 μM (1000 nM) |

As can be seen in FIG. 9, the ACE2 receptor emitted a fluorescence signal (Sample 9B). Upon addition of the Spike Protein (Sample 9C), the fluorescence signal decreased, indicating that the Spike Protein inhibited the ACE2 receptor. Upon further addition of S-Cetirizine (Samples 9D, 9E, 9F, and 9G), the fluorescence signal further decreased. It is believed, without being construed as limiting, that the fluorescence signal results from Samples 9D through 9G suggests that addition of S-Cetirizine modulates the ACE2 receptor, such that S-Cetirizine may be an ACE2 receptor inhibitor, an ACE2 receptor activator, or a combination thereof. Such modulation is believed to influence the interaction between a Spike Protein and the ACE2 receptor (e.g., interfere with/prevent the binding of the Spike Protein and the ACE2 receptor).

R-Cetirizine

Figure 10:
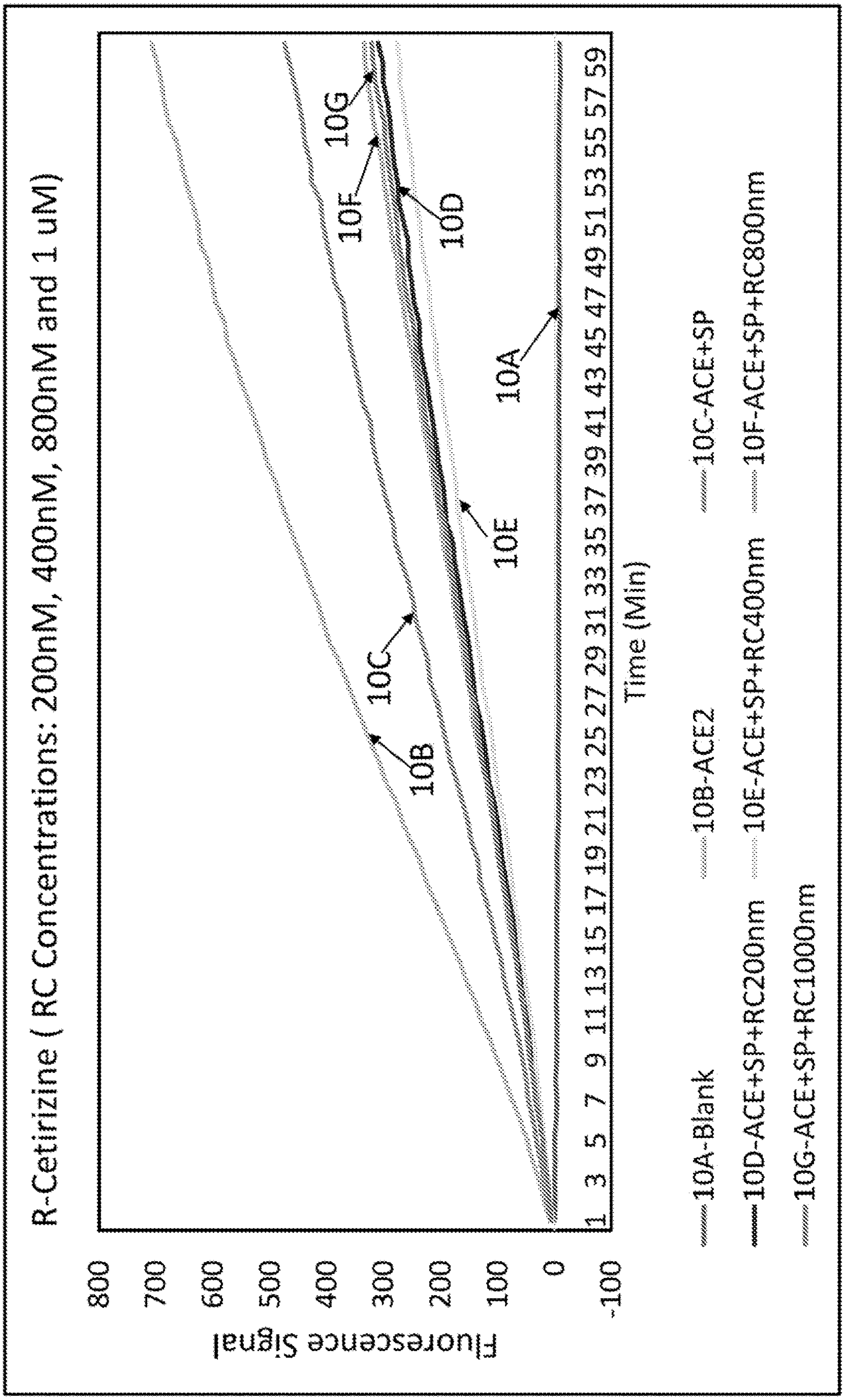
FIG. 10 illustrates ACE2 modulation activity of R-Cetrizine.

In FIG. 10, the fluorescent signal of seven samples were assessed over a duration of 60 minutes. The composition of the samples is summarized in Table 27 below.

TABLE 26

| No. | Sample |
|---|---|
| 10A | Blank |
| 10B | ACE2 Receptor |
| 10C | ACE2 receptor mixed with 3 μL of the Spike Protein |
| 10D | ACE2 receptor mixed with 3 μL of the Spike Protein and R-Cetirizine at an amount effective to arrive at a concentration of 200 nM |
| 10E | ACE2 receptor mixed with 3 μL of the Spike Protein and R-Cetirizine at an amount effective to arrive at a concentration of 400 nM |

TABLE 26-continued

| No. | Sample |
| --- | --- |
| 10F | ACE2 receptor mixed with 3 μL of the Spike Protein and R-Cetirizine at an amount effective to arrive at a concentration of 800 nM |
| 10G | ACE2 receptor mixed with 3 μL of the Spike Protein and R-Cetirizine at an amount effective to arrive at a concentration of 1 μM (1000 nM) |

As can be seen in FIG. 10, the ACE2 receptor emitted a fluorescence signal (Sample 10B). Upon addition of the Spike Protein (Sample 10C), the fluorescence signal decreased, indicating that the Spike Protein inhibited the ACE2 receptor. Upon further addition of R-Cetirizine (Samples 10D, 10E, 10F, and 10G), the fluorescence signal further decreased. It is believed, without being construed as limiting, that the fluorescence signal results from Samples 10D through 10G suggests that addition of R-Cetirizine modulates the ACE2 receptor, such that R-Cetirizine may be an ACE2 receptor inhibitor, an ACE2 receptor activator, or a combination thereof. Such modulation is believed to influence the interaction between a Spike Protein and the ACE2 receptor (e.g., interfere with/prevent the binding of the Spike Protein and the ACE2 receptor).

Example 3

Influence of Antihistamines on Spike Protein's Ability to Penetrate Cells

The results of example 2 illustrated that, in certain embodiments, various antihistamines (e.g., Diphenhydramine, R-Azelastine, S-Azelastine, Hydroxyzine, S-Cetrizine, and R-Cetrizine) act as ACE2 Receptor modulators that may influence the interaction of the Spike Protein with the ACE2 Receptor.

In this example, the ability of one or more antihistamine (s) to influence the ability of the Spike Protein to enter cells through the ACE2 Receptor was assessed. The experimental design was as follows:

1) VERO-E6 cells were grown in dishes
2) The cells were treated with the drug for a few hours
3) The spike protein was added to the cells that were treated with the drug
4) After 12 hours, the cells were lysed and analyzed for the spike protein using Western Blot Vero cells obtained from ATCC were grown in 6 well plates. VERO-E6 cells are kidney cells taken from a monkey, which is considered a suitable assay to assess the entry of the coronavirus (or spike protein) into the cell. At 80% confluency, the cells were treated with various drugs (100 μM of Diphenhydramine, 100 μM of R-Cetirizine, 100 μM of R-Azelastine, and 100 μM of Hydroxyzine) for a period of 6 hours in the absence of fetal bovine serum (FBS). Following 6 hours of drug treatment, the cells were incubated with the SARS Cov2 spike protein (30 ug) for 12 hours. The cells were lysed for extracting the protein. Immunoblotting was carried out using the extracted protein from the cells. The positive control included incubating the cells with the SARS Cov2 spike protein (without the drug pre-treatment step). The negative control included cells that were not treated with a drug or a SARS Cov2 spike protein.

Figure 11:
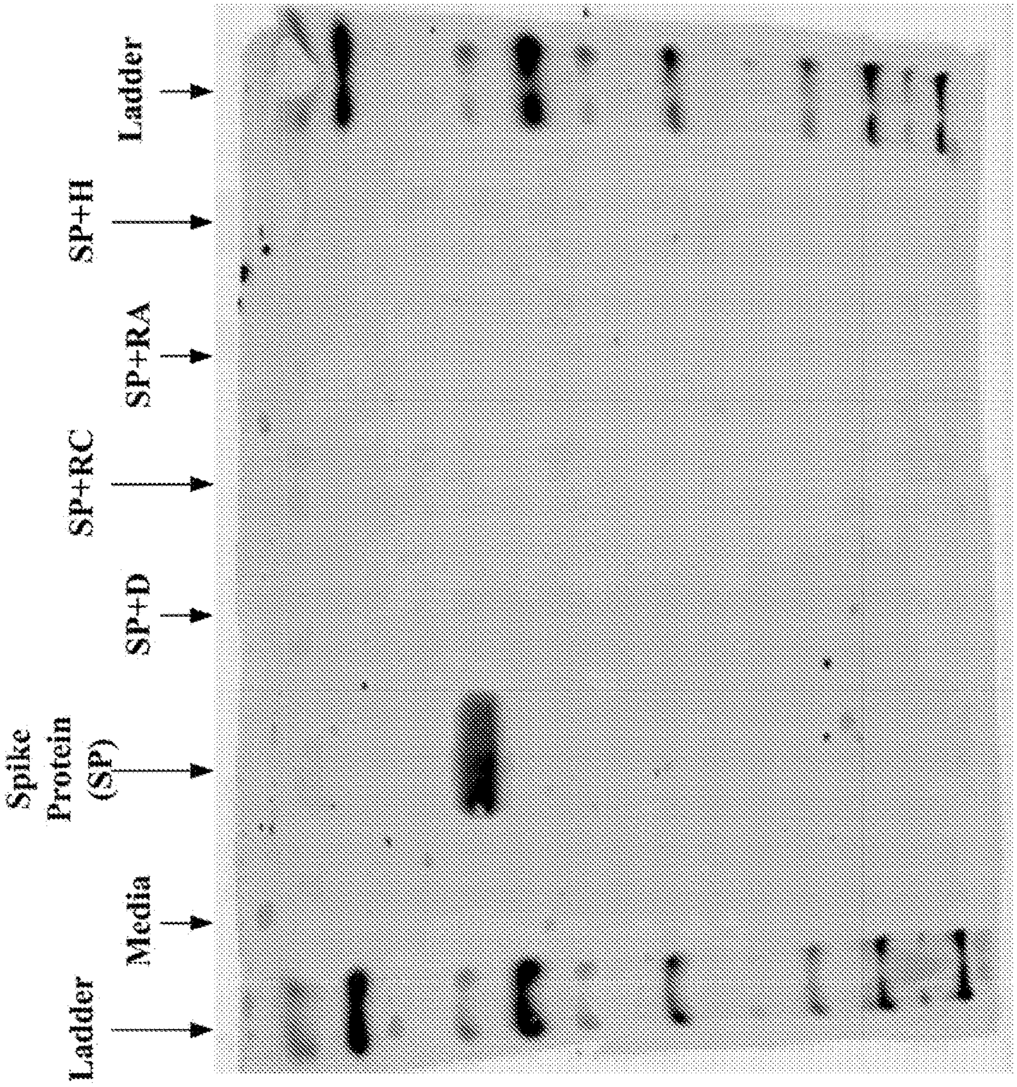
FIG. 11 illustrates western blot image as obtained pursuant to the experiment described in Example 3.

As seen in the western blot image in FIG. 11, the negative control (Media) revealed no spike protein, the positive control (Spike Protein (SP) revealed a high concentration of spike protein in the cell lysate, and the drug treated cells (SP+D, SP+RC, SP+RA, and SP+H) revealed no spike protein (SP) in the cell lysates. The absence of spike protein in the cell lysate samples from the drug treated cells implying that drug treatment inhibited the entry of the spike protein into the cells.

Western Blotting

Spike protein in the supernatant media will be analyzed on 4 to 15% SDS-acrylamide gels and transferred to nitrocellulose membranes. The blot was blocked, and proteins were detected using thr fluorescent method (LICOR).

Example 4

Prophetic Example

In one prophetic example, a patient is treated for COVID-19 with an aerosolized pharmaceutical composition comprising between 20 and 1000 mg of cetirizine (dextrocetirizine, levocetirizine, or a pharmaceutically acceptable salt thereof, or a combination thereof) via pulmonary administration.

Example 5

Prophetic Example

In one prophetic example, a patient is treated for COVID-19 with a pharmaceutical composition comprising between 0.05 mg and 0.5 mg per spray of azelastine hydrochloride (S-azelastine, R-azelastine, or a pharmaceutically acceptable salt thereof, or a combination thereof) via nasal administration.

Example 6

Prophetic Example

In one prophetic example, a patient is treated for COVID-19 with a pharmaceutical composition comprising between 10 mg and 200 mg per diphenydramine hydrochloride via oral administration of a tablet or a capsule or via parenteral administration.

A number of embodiments of the invention have been described. Nevertheless, it will be understood that various modifications may be made without departing from the spirit and scope of the invention. Accordingly, other embodiments are within the scope of the following claims. It should be apparent, however, to those skilled in the art that many more modifications besides those already described are possible without departing from the inventive concepts herein. The inventive subject matter, therefore, is not to be restricted except in the spirit of the disclosure.

All patents, patent publications and publications mentioned herein are incorporated herein by reference in their entirety to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

What is claimed is:

1. A method of treating coronavirus related adverse events comprising administering to a patient in need thereof a therapeutically effective amount of an angiotensin-converting enzyme 2 (ACE2) receptor inhibitor, wherein the ACE2 receptor inhibitor modulator is hydroxyzine, cetirizine, azelastine, fexofenadine, loratadine, diphenhydramine, chloropheniramine, brompheniramine, olopatadine, ketotifen, famotidine, cimetidine, ranitidine, clemastine, desloratadine, rupatadine, carbinoxamine, triprolidine, astemizole, levocabastine, bepotasine, ebastine, nizatidine, benazepril, captopril, enalapril, fosinopril, lisinopril, moexipril, perindopril, quinapril, ramipril, trandolapril, pharmaceutically acceptable salts thereof, or combinations thereof;

wherein the coronavirus related adverse events are pulmonary, cardiac, dermatologic, gastrointestinal, renal, hepatic, endocrine, neurological, or a combination thereof; and wherein the ACE2 receptor inhibitor is administered by route comprising oral, intravenous, nasal, inhalational, topical, buccal, rectal, pleural, peritoneal, vaginal, intramuscular, subcutaneous, transdermal, epidural, intratrachael, otic, intraocular, or intrathecal route.

2. The method of claim 1, wherein the ACE2 receptor inhibitor exhibits a higher affinity for the ACE2 receptor than the ACE1 receptor.

3. The method of claim 2, wherein the ACE2 receptor inhibitor exhibits affinity for the ACE2 receptor ranging from about 2 times to about 100 times greater than its affinity for the ACE1 receptor.

4. The method of claim 1, wherein the ACE2 receptor inhibitor is administered via oral inhalative administration or intranasal administration.

5. A method of treating coronavirus related adverse events comprising administering to a patient in need thereof a therapeutically effective amount of an angiotensin-converting enzyme 2 (ACE2) receptor inhibitor, wherein the ACE2 receptor inhibitor modulator is hydroxyzine, cetirizine, azelastine, fexofenadine, loratadine, diphenhydramine, chloropheniramine, brompheniramine, olopatadine, ketotifen, famotidine, cimetidine, ranitidine, clemastine, desloratadine, rupatadine, carbinoxamine, triprolidine, astemizole, levocabastine, bepotasine, ebastine, nizatidine, benazepril, captopril, enalapril, fosinopril, lisinopril, moexipril, perindopril, quinapril, ramipril, trandolapril, pharmaceutically acceptable salts thereof, or combinations thereof;

wherein the coronavirus related adverse events are pulmonary, cardiac, dermatologic, gastrointestinal, renal, hepatic, endocrine, neurological, or a combination thereof; and wherein the ACE2 receptor inhibitor is administered via a pulmonary route.

6. A method of treating coronavirus related adverse events comprising administering to a patient in need thereof a therapeutically effective amount of an angiotensin-converting enzyme 2 (ACE2) receptor inhibitor, wherein the ACE2 receptor inhibitor modulator is hydroxyzine, cetirizine, azelastine, fexofenadine, loratadine, diphenhydramine, chloropheniramine, brompheniramine, olopatadine, ketotifen, famotidine, cimetidine, ranitidine, clemastine, desloratadine, rupatadine, carbinoxamine, triprolidine, astemizole, levocabastine, bepotasine, ebastine, nizatidine, benazepril, captopril, enalapril, fosinopril, lisinopril, moexipril, perindopril, quinapril, ramipril, trandolapril, pharmaceutically acceptable salts thereof, or combinations thereof;

wherein the coronavirus related adverse events are pulmonary, cardiac, dermatologic, gastrointestinal, renal, hepatic, endocrine, neurological, or a combination thereof; and wherein the ACE2 receptor inhibitor is administered by route comprising oral, intravenous, nasal, inhalational, topical, buccal, rectal, pleural, peritoneal, vaginal, intramuscular, subcutaneous, transdermal, epidural, intratrachael, otic, intraocular, or intrathecal route;

provided that the ACE2 receptor inhibitor is permeable to the blood brain barrier.

* * * * *